US011046958B2

United States Patent
Lakdawala et al.

(10) Patent No.: US 11,046,958 B2
(45) Date of Patent: Jun. 29, 2021

(54) ANTISENSE OLIGONUCLEOTIDES THAT INHIBIT INFLUENZA VIRUS REPLICATION AND USES THEREOF

(71) Applicant: University of Pittsburgh—Of the Commonwealth System of Higher Education, Pittsburgh, PA (US)

(72) Inventors: Seema S. Lakdawala, Pittsburgh, PA (US); Nara Lee, Pittsburgh, PA (US)

(73) Assignee: University of Pittsburgh - Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 16/480,240

(22) PCT Filed: Jan. 22, 2018

(86) PCT No.: PCT/US2018/014698
§ 371 (c)(1),
(2) Date: Jul. 23, 2019

(87) PCT Pub. No.: WO2018/140354
PCT Pub. Date: Aug. 2, 2018

(65) Prior Publication Data
US 2019/0367923 A1 Dec. 5, 2019

Related U.S. Application Data

(60) Provisional application No. 62/449,712, filed on Jan. 24, 2017.

(51) Int. Cl.
*C12N 15/113* (2010.01)
*A61K 9/00* (2006.01)

(52) U.S. Cl.
CPC ........ *C12N 15/1131* (2013.01); *A61K 9/0029* (2013.01); *A61K 9/0053* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3233* (2013.01)

(58) Field of Classification Search
None
See application file for complete search history.

(56) References Cited

U.S. PATENT DOCUMENTS

| 5,580,767 A | 12/1996 | Cowsert et al. |
| 5,952,490 A | 9/1999 | Hanecak et al. |
| 2011/0033859 A1 | 2/2011 | de Fougerolles et al. |
| 2011/0118334 A1 | 5/2011 | Iversen |
| 2013/0267429 A1* | 10/2013 | Gardner ............... G16B 25/00 |
| | | 506/8 |

FOREIGN PATENT DOCUMENTS

WO WO 2006/047683 5/2006

OTHER PUBLICATIONS

Evers et al., "Antisense Oligonucleotides in Therapy for Neurodegenerative Disorders," *Adv. Drug Deliv. Rev.*, vol. 87:90-103, 2015.
Lee et al., "Genome-wide analysis of influenza viral RNA and nucleoprotein association," *Nucleic Acids Res.*, vol. 45(15):8968-8977, 2017.
Lenartowicz et al., "Antisense Oligonucleotides Targeting Influenza A Segment 8 Genomic RNA Inhibit Viral Replication," *Nucleic Acid Ther.*, vol. 26:277-285, 2016.
Prakash et al, "Targeted Delivery of Antisense Oligonucleotides to Hepatocytes using Triantennary N-acetyl Galactosamine Improves Potency 10-fold in Mice," *Nucleic Acids Res.*, vol. 42:8796-8807, 2014.
Soszynska-Jozwiak et al., "A Conserved Secondary Structural Element in the Coding Region of the Influenza A Virus Nucleoprotein (NP) mRNA is Important for the Regulation of Viral Proliferation," *PLoS One*, vol. 10:e0141132, 2015.

* cited by examiner

*Primary Examiner* — Tracy Vivlemore
(74) *Attorney, Agent, or Firm* — Klarquist Sparkman, LLP

(57) ABSTRACT

Antisense oligonucleotides (ASOs) that disrupt RNA-RNA interactions of influenza virus genome segments that are required for virus packaging are described. The ASOs can be used to inhibit influenza A virus replication in vitro and in vivo. Use of the ASOs for the treatment of a subject with an influenza virus infection is also described.

20 Claims, 24 Drawing Sheets

Specification includes a Sequence Listing.

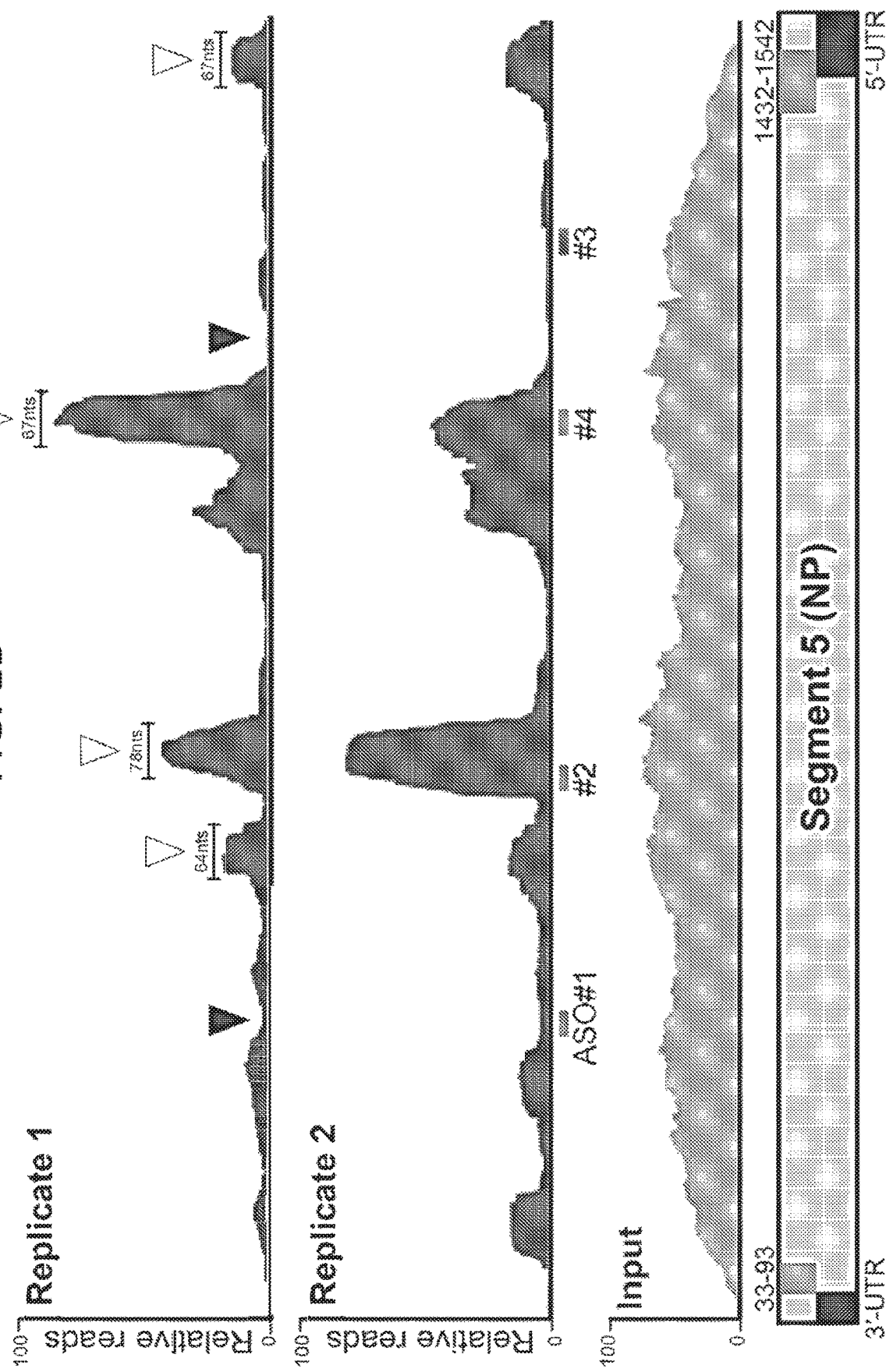

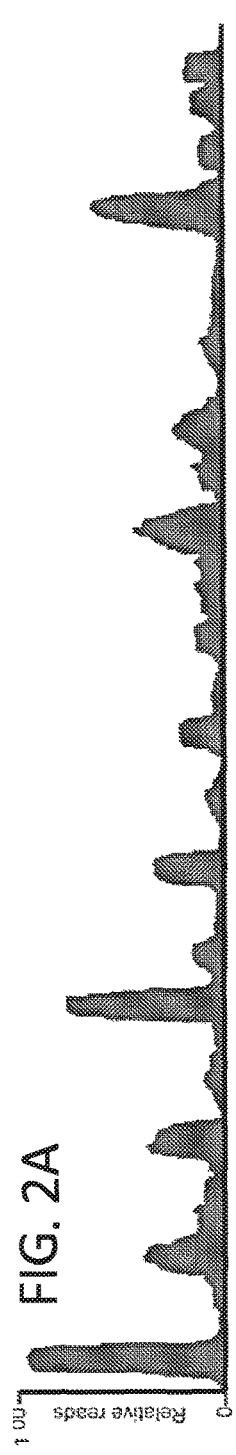
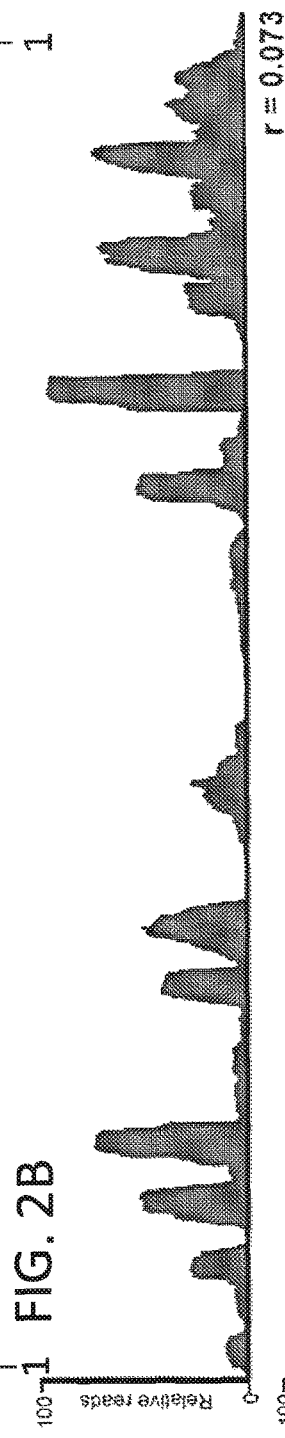
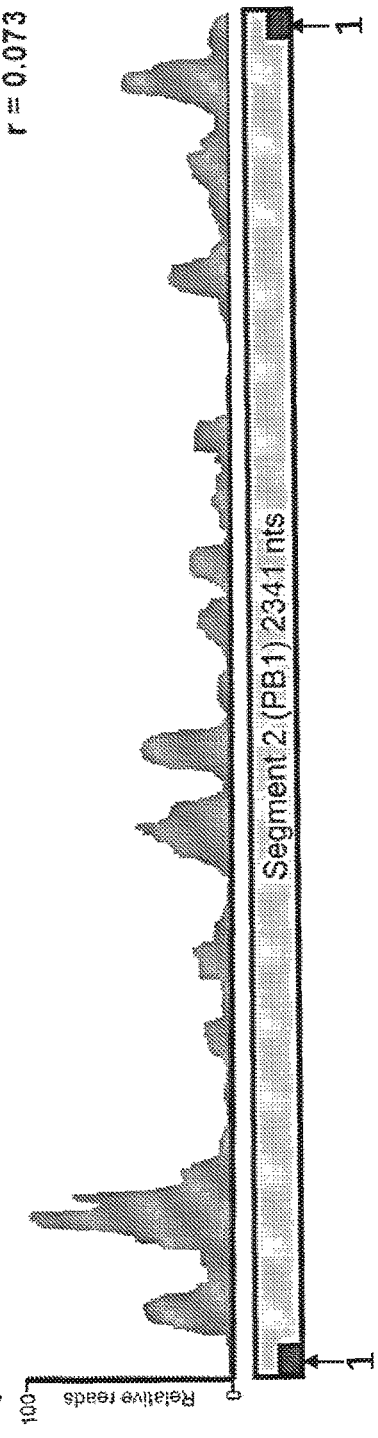
FIG. 2A
FIG. 2B

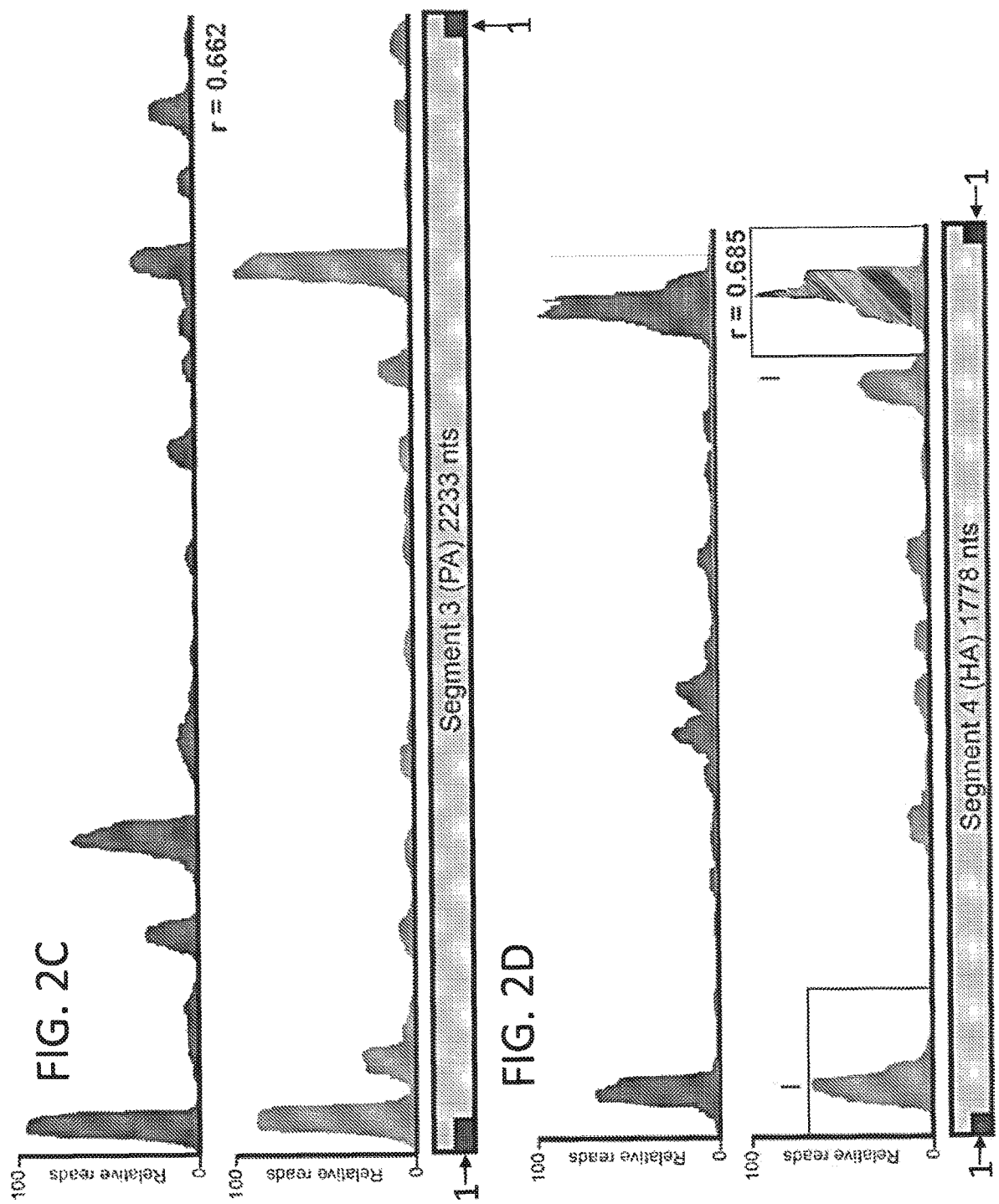

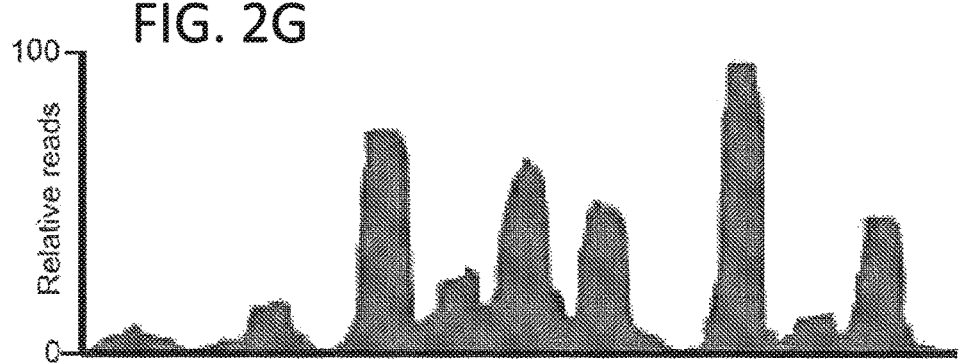
FIG. 2G
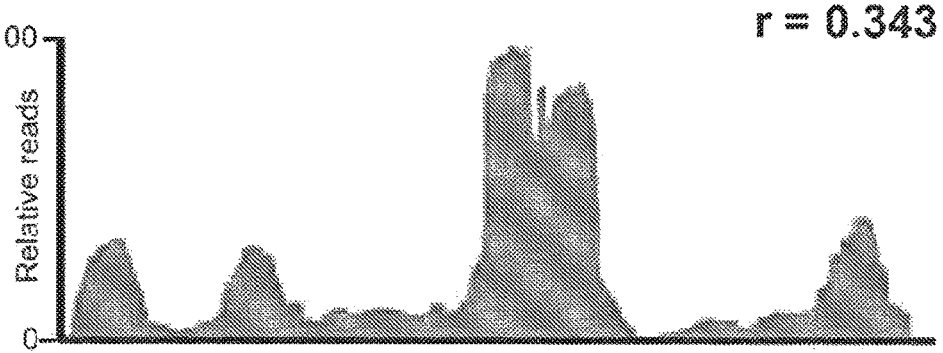
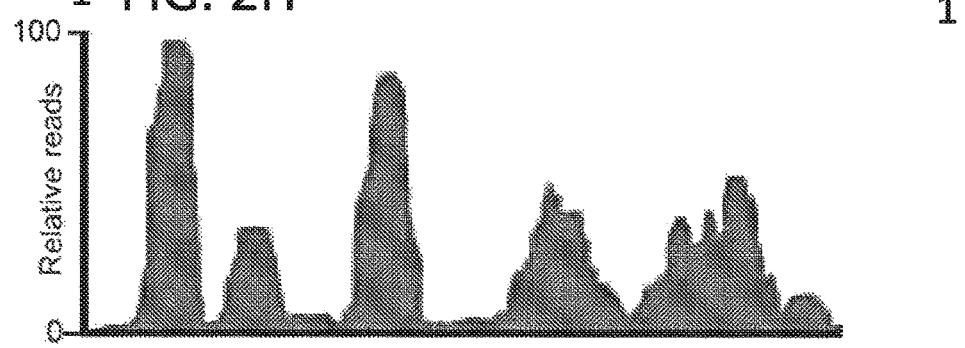
FIG. 2H
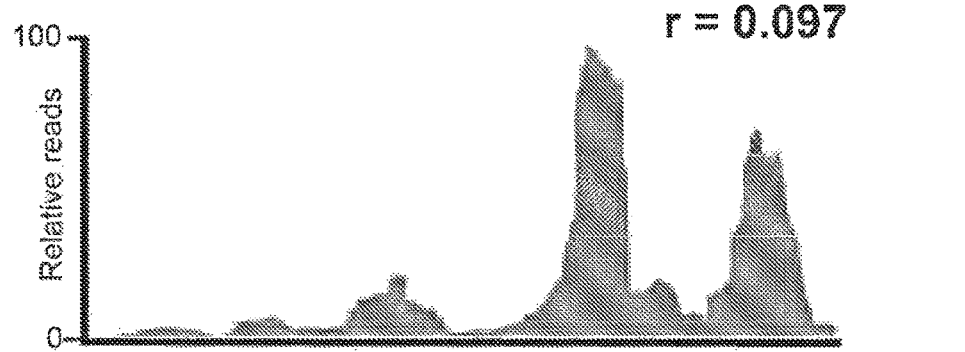

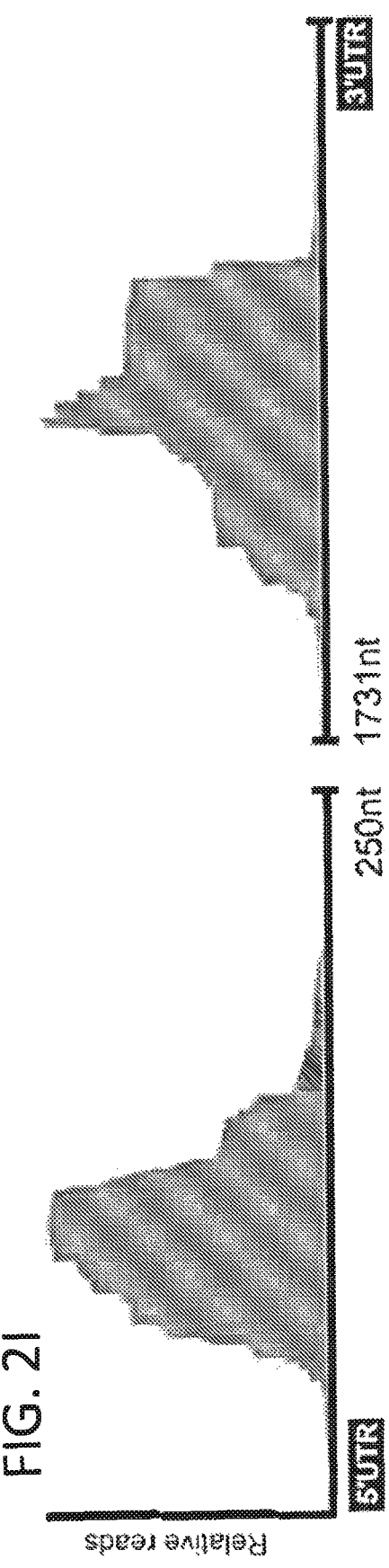
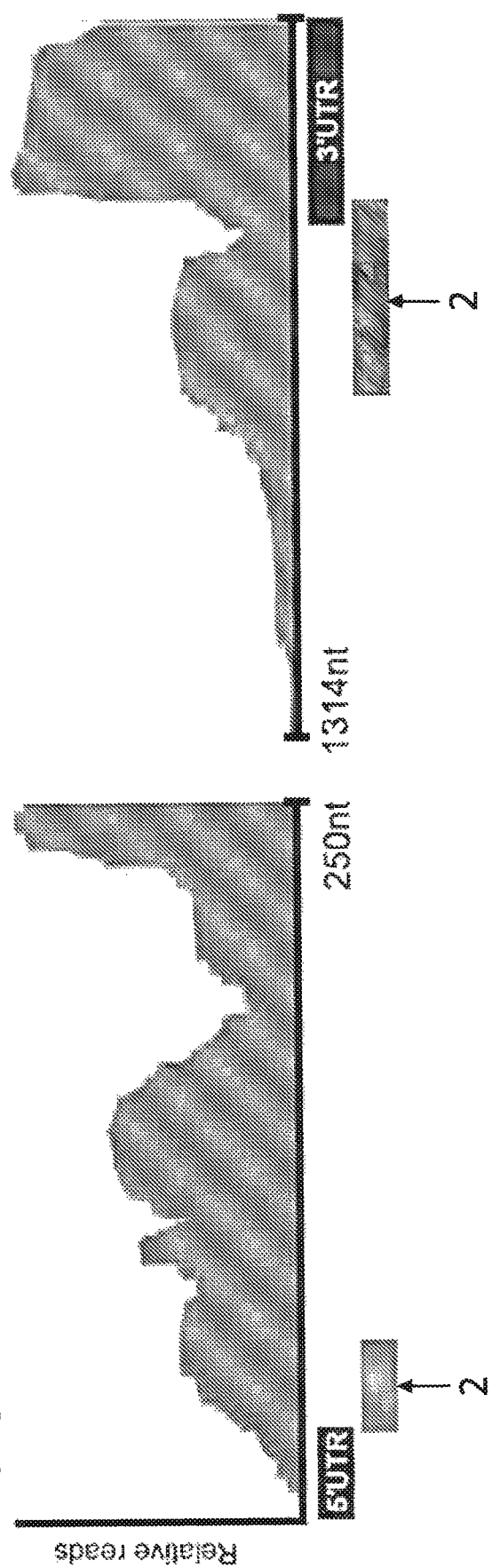
FIG. 2I
FIG. 2J

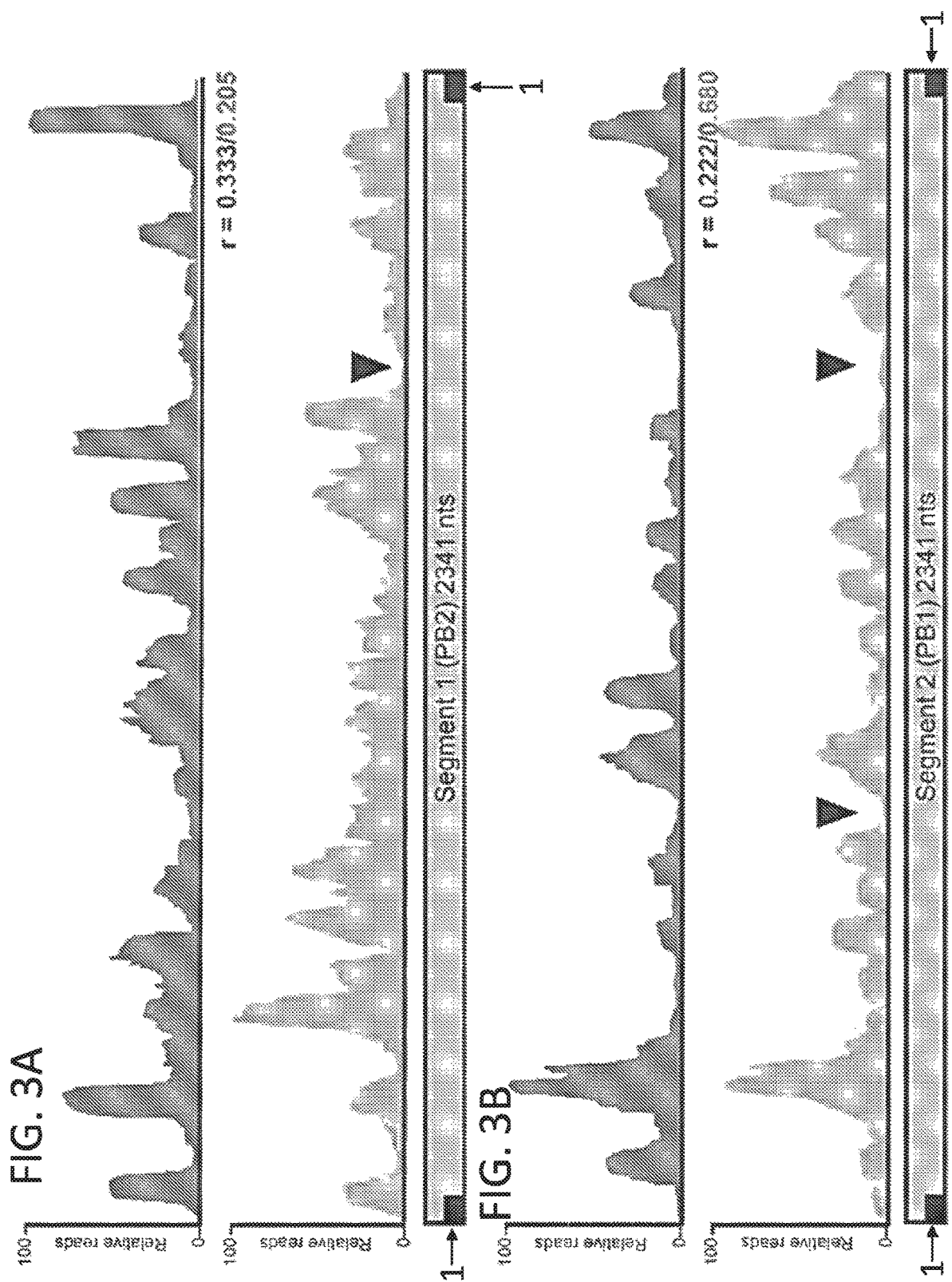

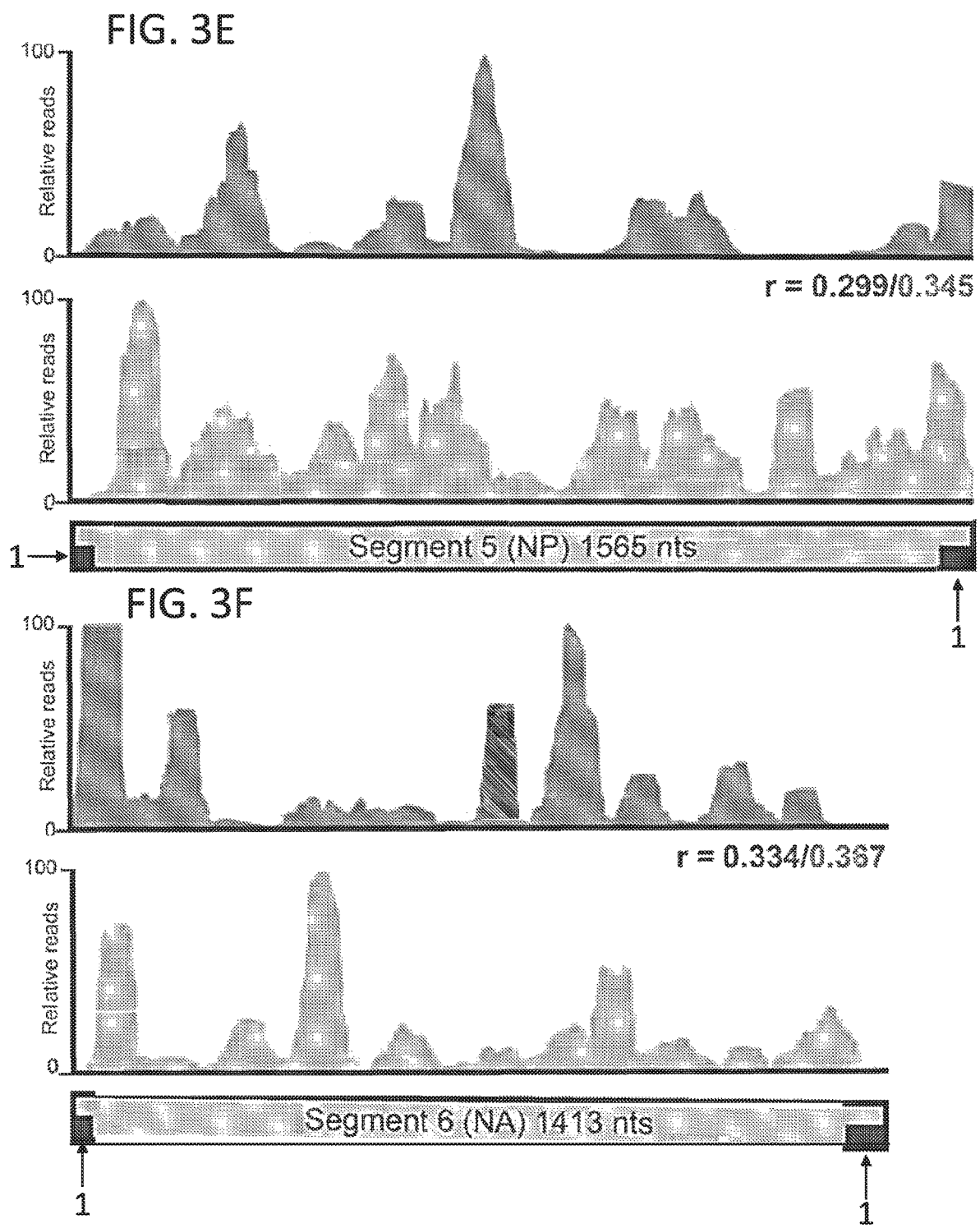

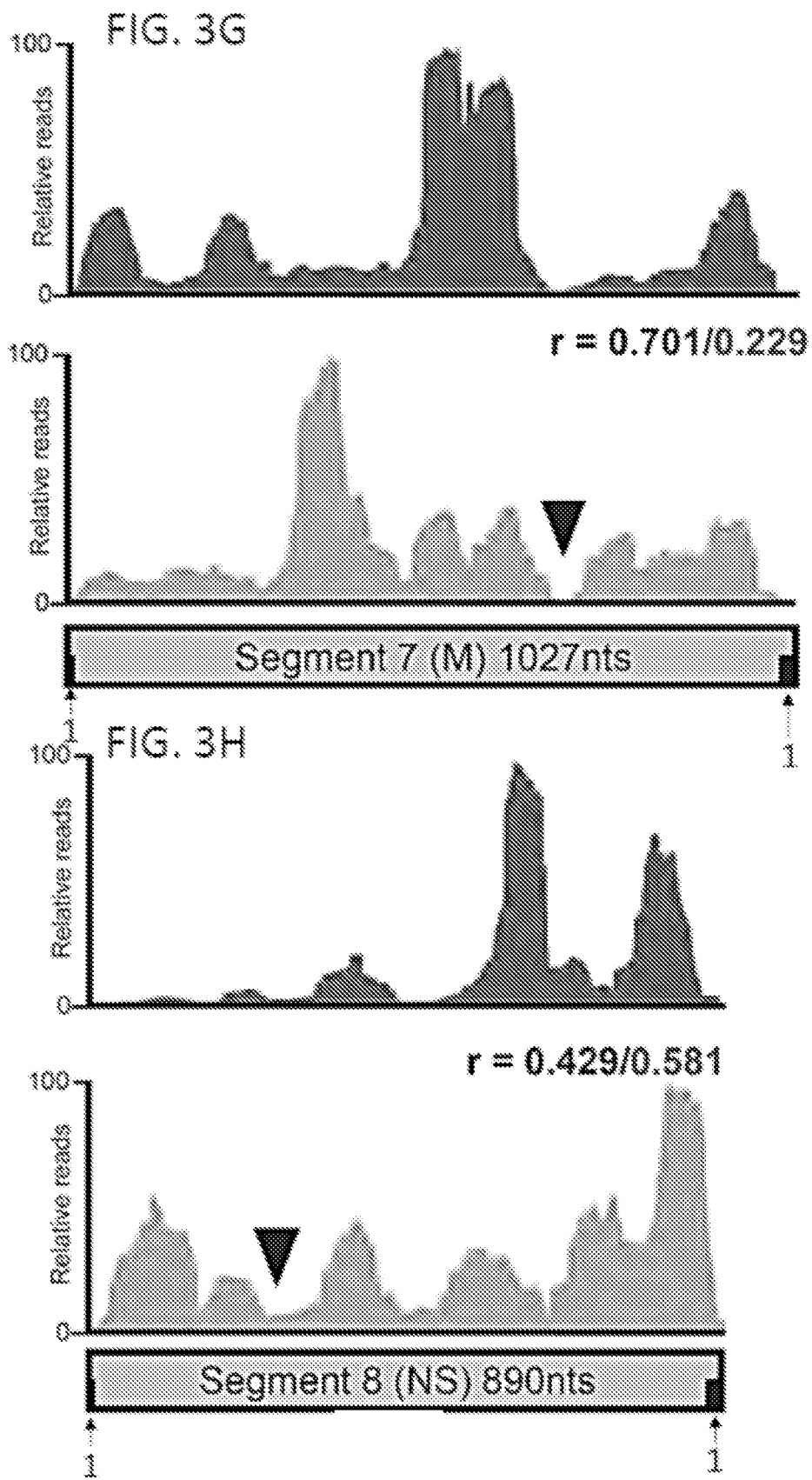

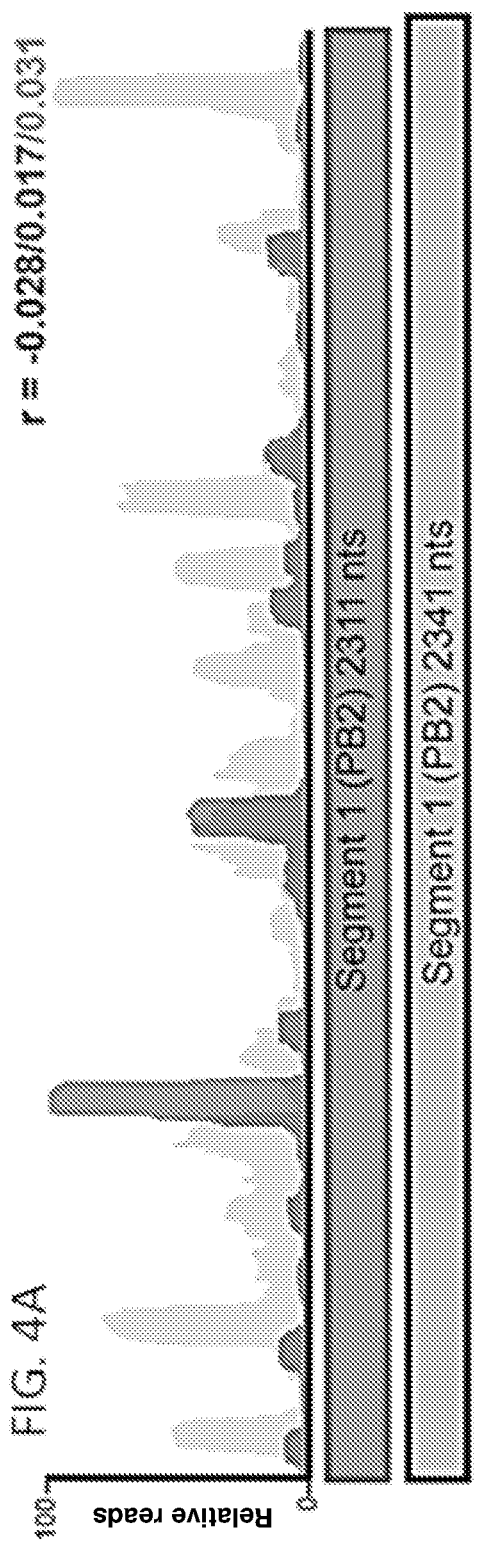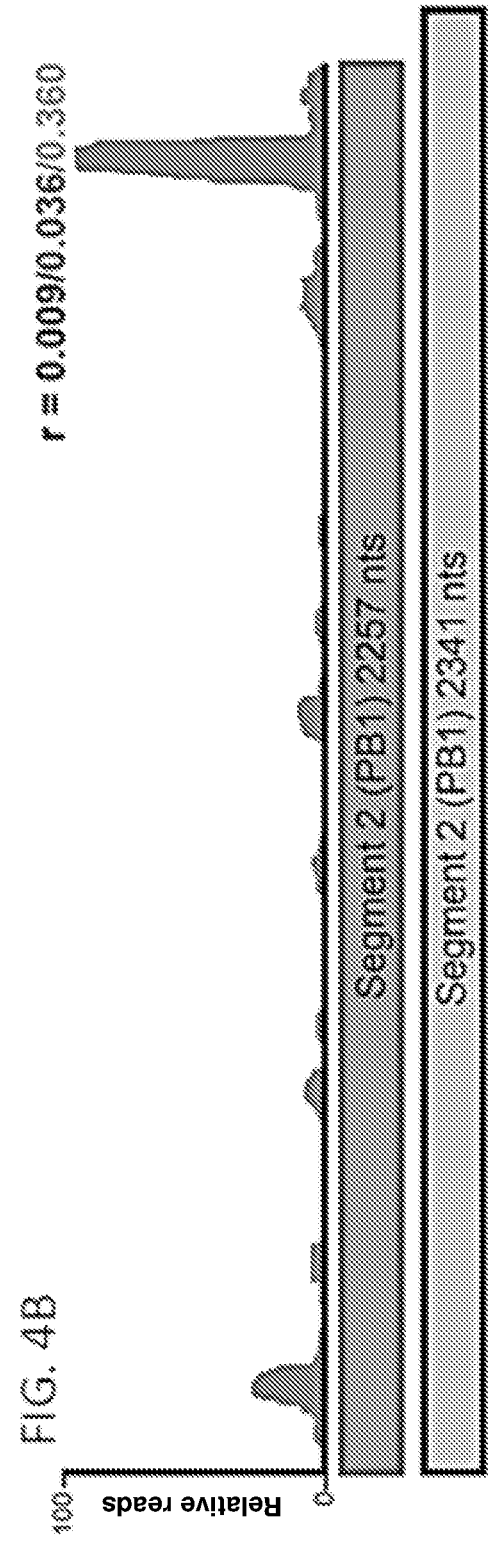
FIG. 4A
FIG. 4B

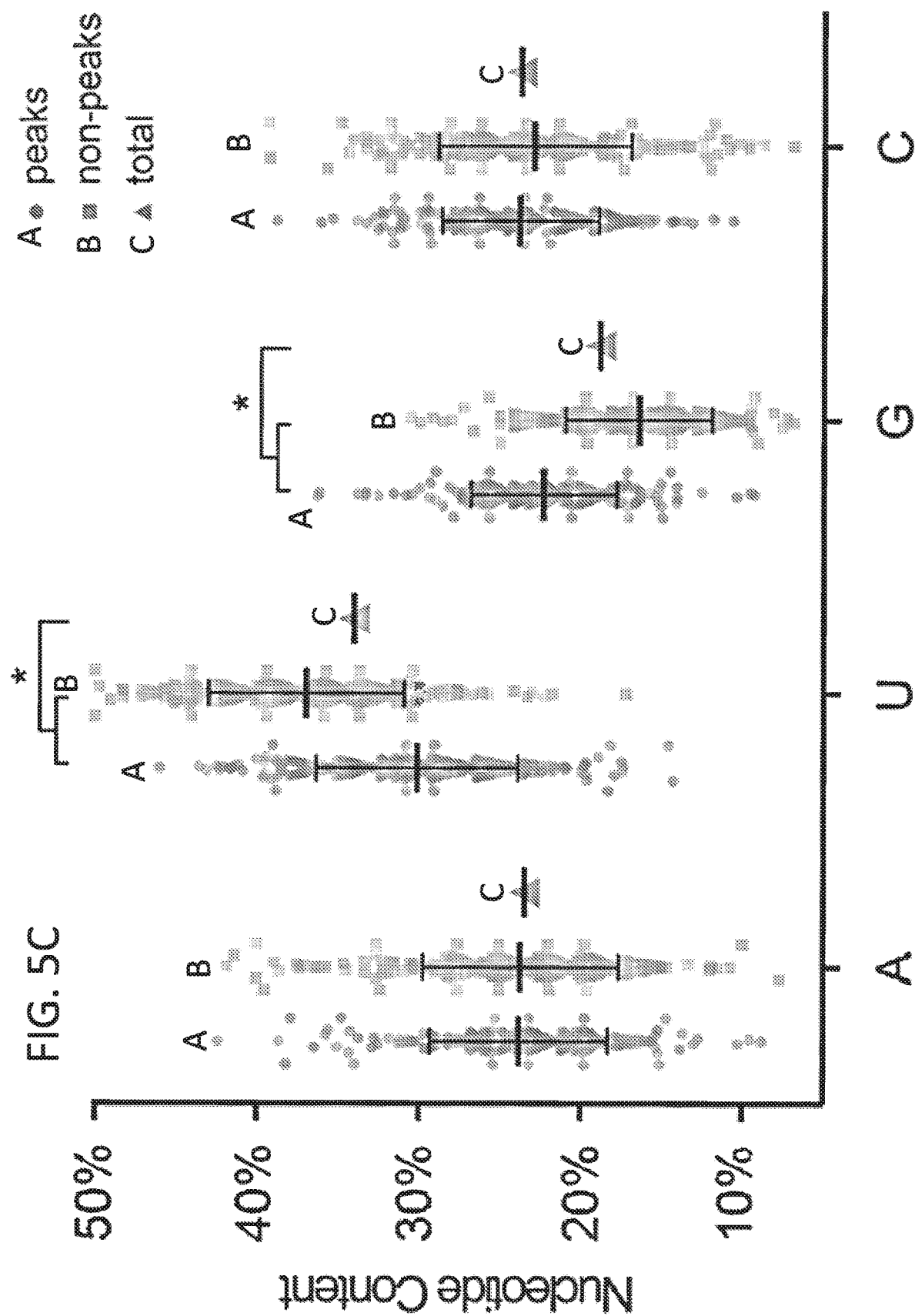

| Strain | # of Peaks | Peaks w/o Doublets | Mean Peak Width (nts) |
|---|---|---|---|
| WSN | 47 | 41 | 62.5 ± 15.3 |
| H1N1pdm | 45 | 43 | 72.7 ± 24.7 |
| H3N2 | 46 | 37 | 67.6 ± 23.3 |
| IBV | 40 | 33 | 74.8 ± 24.8 |

ANTISENSE OLIGONUCLEOTIDES THAT INHIBIT INFLUENZA VIRUS REPLICATION AND USES THEREOF

CROSS REFERENCE TO RELATED APPLICATIONS

This application is the U.S. National Stage of International Application No. PCT/US2018/014698, filed Jan. 22, 2018, published in English under PCT Article 21(2), which claims the benefit of U.S. Provisional Application No. 62/449,712, filed Jan. 24, 2017, which is herein incorporated by reference in its entirety.

FIELD

This disclosure concerns antisense oligonucleotides (ASOs) than inhibit influenza A virus replication and use of the ASOs for the treatment of influenza virus infection.

BACKGROUND

Influenza A and B viruses (JAY, IBV) pose a substantial public health burden through frequent epidemics and occasional pandemics in humans. Pandemic influenza viruses emerge through reassortment of human and animal influenza viruses or direct transmission of animal influenza viruses. IAV are endemic in multiple animal species from wild birds to domestic chickens and pigs; these animal reservoirs provide opportunities for viral evolution and reassortment to produce novel pandemic influenza viruses. For example, the 2009 H1N1 pandemic (H1N1pdm), that killed over 200,000 people emerged through reassortment of two swine influenza viruses and was capable of spreading readily human-to-human. To define the molecular barriers dictating IAV reassortment and emergence of pandemic influenza viruses, a more detailed understanding of the intracellular assembly of the viral genome is required.

Influenza viruses contain eight, negative-sense, single-stranded RNA segments that are named according to the primarily encoded protein: PB2, PB1, PA, HA, NP, NA, M and NS. All viral RNA (vRNA) genome segments associate with multiple copies of nucleoprotein (NP) and the viral RNA-dependent RNA polymerase (composed of PB2, PB1 and PA) to form a viral ribonucleoprotein (vRNP) complex. Additionally, all vRNA segments share conserved sequences at the 5' and 3' untranslated regions (UTRs), which promote association with the viral polymerase complex (Coloma, *PLoS Pathog* 5(6):e1000491, 2009). Incorporation of all eight vRNPs is necessary for production of fully infectious influenza virus (Hatada et al., *J Biochem* 105(4):537-546, 1989; McGeoch et al., *Proc Natl Acad Sci USA* 73(9):3045-3049, 1976). Recent reports have suggested that assembly of all eight segments occurs en route to the plasma membrane for packaging (Lakdawala et al., *PLoS Pathog* 10(3): e1003971, 2014; Chou et al., *PLoS Pathog* 9(5):e1003358, 2013). Although the mechanism of selective assembly remains unknown, there is evidence suggesting that the process is driven by RNA-RNA interactions (Essere et al., *Proc Natl Acad Sci USA* 110(40):E3840-3848, 2013; Fournier et al., *Vaccine* 39(51):7359-7367, 2012; Fournier et al., *Nucleic Acids Res* 40(5):2197-2209, 2012; Gavazzi et al., *Nucleic Acids Res* 41(2):1241-1254, 2013; Gavazzi et al., *Proc Natl Acad Sci USA* 110(41):16604-16609, 2013; Noda et al., *Nat Commun* 3:639, 2012).

Many published studies have demonstrated that the 5' and 3' ends of vRNA coordinate packaging and bundling of all eight segments (Fujii et al., *J Viral* 79(6):3766-3774, 2005; Fujii et al., *Proc Natl Acad Sci USA* 100(4):2002-20072003; Liang et al., *J Virol* 79(16):10348-10355, 2005; Muramoto, *J Virol* 80(5):2318-2325, 2006; Ozawa et al., *J Virol* 81:430-441, 2007; Watanabe et al., *J Virol* 77(19):10575-10583, 2003; Dos Santos Afonso et al., *Virology* 341(1):34-46, 2005; Ozawa et al., *J Virol* 83(7):3384-3388, 2009; Goto, *J Virol* 87(21):11316-11322, 2013). However, no direct interactions between these ends have been observed. Alternatively, in vitro RNA binding assays have suggested that regions within different vRNA segments can form RNA-RNA interactions (Gilbertson et al., *Viruses* 8:8, 2016; Gavazzi et al., *Nature* 456(7221):464-469, 2013). Such interactions may be important to further our understanding of selective assembly and reassortment of influenza viruses, but an in vivo RNA interaction map has not yet been described.

Cryo-electron microscopy (EM) reconstructions indicated that the vRNP is a double helical hairpin structure with two anti-parallel strands, which are held together through NP-NP interactions on opposing strands (Arranz et al., *Science* 338(6114):1634-1637, 2012; Moeller et al., *Science* 338 (6114):1631-1634, 2012). Mass spectrometry analysis of purified influenza virions, indicates that approximately 66 NP molecules are present for each packaged polymerase, i.e., each segment (Hutchinson et al., *Nat Commun* 5:4816, 2014). EM and tomography studies have demonstrated that vRNPs are arranged in a "7+1" pattern, with a single vRNP segment in the center surrounded by the other seven vRNP segments (Fournier et al., *Nucleic Acids Res* 40(5):2197-2209, 2012; Noda et al., *Nat Commun* 3:639, 2012). This ordered assembly of vRNP segments compliments the notion that a mechanism facilitates selective assembly of influenza viruses. In addition, the NP RNA binding groove of NP interacts with the RNA backbone, resulting in the bases facing outward and thus rendering the vRNA accessible for base pairing (Arranz et al., *Science* 338(6114): 1634-1637, 2012; Moeller, et al., *Science* 338(6114):1631-1634, 2012; Baudin et al., *EMBO J* 13(13):3158-3165, 1994). Importantly, every schematic and description of vRNP structures to date portrays a uniform random binding of NP proteins, similar to a beads on a string structure (Eisfeld et al., *Nat Rev Microbiol* 13(1):28-41, 2015; Te Velthuis et al., *Nat Microbial* 1:16029, 2016; Cros and Palese, *Virus Res* 95(1-2):3-12, 2003; Whittaker et al., *Trends Cell Biol* 6(2):67-71, 1996; Wu et al., *J Mol Biol* 374(4):910-916, 2007), neglecting the possibility that vRNA segments may produce large secondary structures in the internal region to mediate RNA-RNA interactions.

SUMMARY

Disclosed herein are ASOs that bind to conserved regions of the influenza A virus genome that are involved in RNA-NP interactions required for virus packaging. The ASOs inhibit virus replication and can be used as a treatment for influenza A virus infection.

Provided herein are compositions that include at least one inhibitory ASO. In some embodiments, the at least one ASO is at least 90% identical to SEQ ID NO: 1, SEQ ID NO: 2, SEQ ID NO: 3, SEQ ID NO: 4, SEQ ID NO: 5 and/or SEQ ID NO: 6. In some embodiments, the at least one ASO comprises at least 20, at least 25 or at least 30 consecutive nucleotides of SEQ ID NO: 1, SEQ ID NO: 2, SEQ ID NO: 3, SEQ ID NO: 4, SEQ ID NO: 5 and/or SEQ ID NO: 6. In some embodiments, the composition includes a pharmaceutically acceptable carrier. In some embodiments, the at least one ASO comprises at least one chemical modification.

Further provided herein are methods of inhibiting replication of an influenza A virus in a host cell by contacting the cell with a composition disclosed herein. In some embodiments, the method is an in vitro method. In other embodiments, the method is an in vivo method.

Further provided herein is are methods of treating an influenza A virus infection in a subject by administering to the subject a composition disclosed herein.

The foregoing and other objects, features, and advantages of the invention will become more apparent from the following detailed description, which proceeds with reference to the accompanying figures.

BRIEF DESCRIPTION OF THE DRAWINGS

FIGS. 1A-1C: Influenza A/WSN/33 virus (H1N1) NP binds to specific regions of the viral RNA genome. (FIG. 1A) Schematic representation of the HITS-CLIP protocol. Influenza virus particles were subjected to UV light irradiation (254 nm wavelength) and collected by ultracentrifugation on a 30% sucrose cushion. Virus particles were lysed, subjected to a partial RNase A digestion and immunoprecipitated using an anti-NP antibody. An audioradiogram of $^{32}$P-labelled RNA crosslinked to A/WSN/33 NP is shown. Slower migrating bands in the +UV sample (white dashed box) were excised, and the RNA was isolated. Deep sequencing libraries were generated and mapped to Influenza reference genomes. Two potential outcomes are shown: i) NP binds uniformly to the entire vRNA genome (top); ii) NP binding is enriched at specific regions of the vRNA genome (peaks) and is accompanied by NP-low areas (non-peaks) (bottom). (FIG. 1B) NP binding profile determined by HITS-CLIP for segment 5 (NP) of the WSN strain is shown as a representative. Schematic of segment 5 is shown at the bottom including regions of vRNA important for packaging (UTRs) and bundling (nt 33-93 and 1432-1542). Abundance of RNAseq reads were normalized against the highest peak in each individual vRNA segment and arbitrarily set to 100. The results from two independent HITS-CLIP replicates and control total input RNA are shown. NP binding displayed strong peaks or areas enriched for NP association (open arrowheads, defined using MACS software) and NP-free regions (black arrowhead, where the deep sequencing coverage was similar to background levels). (FIG. 1C) vRNA accessibility assay was performed on WSN viral lysate containing vRNA segments complexed with NP; DNA antisense oligonucleotides (ASO #1-4) were used to target NP-binding sites or NP-low regions of segment 5 (NP) depicted in FIG. 1B. Northern blot analysis for NP segment was carried out to examine accessibility as determined by RNase H digestion. Northern blot against segment 1 (PB2) (control) is also shown.

FIGS. 2A-2J: Comparison of H1N1 IAV NP binding profile. (FIGS. 2A-2H) HITS-CLIP reads of each segment from WSN (top graph in each panel) and H1N1pdm (bottom graph in each panel) are shown. Abundance of RNAseq reads were normalized against the highest peak in each individual vRNA segment and arbitrarily set to 100. Schematic representation of each segment depicts the regions of vRNA important for packaging (1) and bundling (2). Pearson correlation coefficient (r) between WSN and H1N1pdm segment pairs are indicated. (FIG. 2I) The 5' (left) and 3' (right) ends of segment 4 (HA) are devoid of H1N1pdm NP association. (FIG. 2J) The 5' (left) and 3' (right) ends of segment 5 (NP) are H1N1pdm NP-bound.

FIGS. 3A-3H: Comparison of H1N1 and H3N2 NP binding profiles. HITS-CLIP reads of each segment from H1N1pdm (top) and H3N2 (bottom) are shown. Abundance of RNAseq reads were normalized against the highest peak in each individual vRNA segment and arbitrarily set to 100. Regions mediating packaging are indicated (1) in the schematics of each segment. Pearson correlation coefficient (r) between H3N2 and WSN (bottom graph) or H1N1pdm (top graph) is indicated for each segment pair. Select non-peak regions are indicated by black arrowheads.

FIGS. 4A-4H: IBV NP association is significantly different from IAV. HITS-CLIP reads of each IBV segment are shown. Abundance of RNAseq reads were normalized against the highest peak in each individual vRNA segment and arbitrarily set to 100. At the bottom of each figure are schematic representations of the IBV (top bar) and IAV (bottom bar) segments. (FIG. 4A) HITS-CLIP read of IBV segment 1 (PB2). Segment 1 from H1N1pdm is shown as a transparent profile. Pearson correlation coefficient (r) between IBV and WSN=−0.028, IBV and H1N1pdm=0.017, and IBV and H3N2=0.031. (FIG. 4B) HITS-CLIP read of IBV segment 2 (PB1). Pearson correlation coefficient (r) between IBV and WSN=0.009, IBV and H1N1pdm=0.036, and IBV and H3N2=0.360. (FIG. 4C) HITS-CLIP read of IBV segment 3 (PA). Pearson correlation coefficient (r) between IBV and WSN=0.135, IBV and H1N1pdm=0.019, and IBV and H3N2=0.165. (FIG. 4D) HITS-CLIP read of IBV segment 4 (HA). Pearson correlation coefficient (r) between IBV and WSN=0.027, IBV and H1N1pdm=0.241, and IBV and H3N2=0.067. (FIG. 4E) HITS-CLIP read of IBV segment 5 (NP). Pearson correlation coefficient (r) between IBV and WSN=−0.011, IBV and H1N1pdm=−0.103, and IBV and H3N2=0.094. (FIG. 4F) HITS-CLIP read of IBV segment 6 (NA). Pearson correlation coefficient (r) between IBV and WSN=−0.113, IBV and H1N1pdm=0.002, and IBV and H3N2=−0.262. (FIG. 4G) HITS-CLIP read of IBV segment 7 (M). Pearson correlation coefficient (r) between IBV and WSN=−0.215, IBV and H1N1pdm=−0.216, and IBV and H3N2=−0.262. (FIG. 4H) HITS-CLIP read of IBV segment 8 (NS). Pearson correlation coefficient (r) between IBV and WSN=0.394, IBV and H1N1pdm=−0.186, and IBV and H3N2=−0.064.

FIGS. 5A-5C: Characterization of NP HITS-CLIP peaks and non-peaks. Sequence variability of 385 and 353 H1N1 sequences are shown for segment 4 (HA) (FIG. 5A) and segment 6 (NA) (FIG. 5B), respectively. A sliding window algorithm of 20 base-pair windows was used to generate variability plots. Sequences corresponding to NP binding sites conserved between WSN and H1N1pdm are boxed, non-conserved peaks are displayed as shaded boxes. (FIG. 5C) Nucleotide composition of peaks (defined by MACS software) and non-peaks (remaining sequence not contained in peaks) was determined and is plotted as a percentage of the corresponding sequence. All peak and non-peak regions from all eight segments of WSN, H1N1pdm, H3N2, and IBV are included, demonstrating the robustness of the phenotype. The average nucleotide composition for all gene segments from all viruses tested is displayed indicated by a triangle. Asterisk (*) denotes significant difference between nucleotide compositions using a two-way ANOVA test (p-value <0.0001).

(FIG. 8A) The peak-finding algorithm MACS was used to predict NP binding sites. The first row of boxes underneath the HITS-CLIP profile indicate the called peaks. Non-peaks were defined as regions containing less than 5% read coverage of the maximum peak height for each HITS-CLIP experiment. The dashed line indicates the 5% threshold; the second row of boxes denote non-peak regions. For calculating mean peak width, obvious double peaks, as shown for segment 4 (HA), which were called as a single peak by MACS, were excluded from the calculation. (FIG. 8B) The peak width distribution for each influenza strain is shown. A bin size of 20 was used for the predicted peaks by MACS. (FIG. 8C) Summary of data for each influenza virus strain.

SEQUENCE LISTING

Figure 1A:
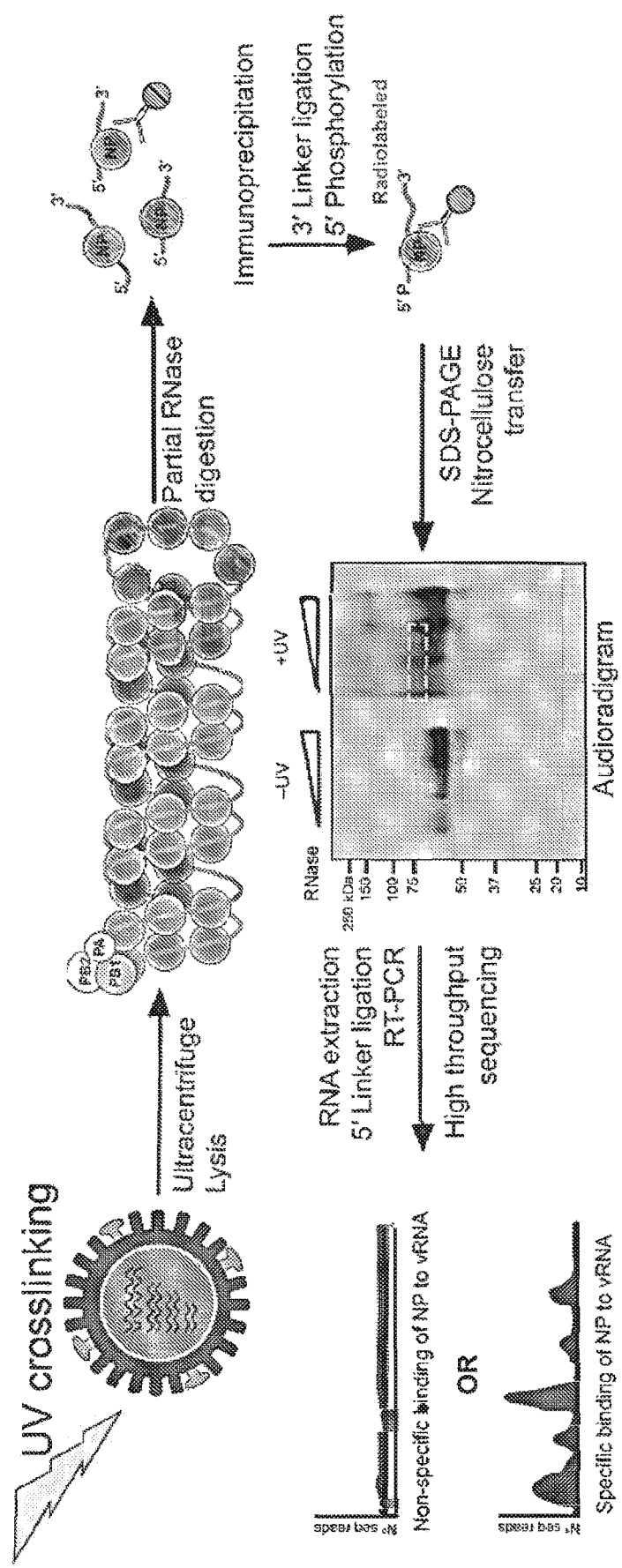

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 19, 2019, 2.5 KB, which is incorporated by reference herein. In the accompanying sequence listing:

SEQ ID NOs: 1-11 are antisense oligonucleotide sequences.

DETAILED DESCRIPTION

I. Abbreviations

ASO antisense oligonucleotide
EM electron microscopy
HA hemagglutinin
HITS-CLIP high-throughput RNA sequencing coupled with crosslinking immunoprecipitation
IAV influenza A virus
IBV influenza B virus
LNA locked nucleic acid
MACS Model-based Analysis for ChIP-Seq
NA neuraminidase
NP nucleoprotein
PBS phosphate buffered saline
PNA peptide nucleic acid
UV ultraviolet
vRNA viral RNA
vRNP viral ribonucleoprotein II. Terms and Methods Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. an ASO), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Antisense oligonucleotide (ASO): A synthetic, single-stranded nucleic acid-based oligomer that is complementary to a target nucleic acid molecule, such as a target RNA. An antisense oligonucleotide can include one or more chemical modifications to the sugar, base, and/or internucleoside linkages. Exemplary modifications to the sugar include, but are not limited to, LNA, 2'-O-methyl, 2'-O-methoxy-ethyl (MOE), 2'-fluoro, cEt and tc-DNA. Modifications to the internucleoside linkages include, for example, phosphorothioate and phosphoramidate. One example of a modified base is 5-methylcytosine.

Contacting: Placement in direct physical association; includes both in solid and liquid form. When used in the context of an in vivo method, "contacting" also includes administering.

Influenza virus: An enveloped virus with a negative-sense RNA genome comprised of 8 genome segments. Influenza viruses are classified in the family Orthomyxoviridae. The three genera of influenza viruses that infect humans are influenza A, influenza B and influenza C. Influenza A viruses infect humans and other mammals, as well as birds. These viruses cause can flu pandemics. Influenza A viruses include a number of different serotypes (or subtypes) that are classified based on their hemagglutinin (HA) and neuraminidase (NA) proteins; sixteen HA subtypes and nine NA subtypes have been identified. Influenza A virus subtypes include, but are not limited to, H1N1, H1N2, H2N2, H3N1, H3N2, H3N8, H5N1, H5N8, H5N9, H7N1, H7N4, H7N7, H7N9, H9N2 and H10N7.

Influenza A virus (IAV): A negative-sense, single-stranded, segmented RNA virus, which has eight RNA segments (PB2, PB1, PA, NP, M, NS, HA and NA) that code for 11 proteins, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2). This virus is prone to rapid evolution by error-protein polymerase and by segment reassortment. The host range of influenza A is diverse, and includes humans, birds (e.g., chickens and aquatic birds), horses, marine mammals, pigs, bats, mice, ferrets, cats, tigers, leopards, and dogs. In animals, most influenza A viruses cause mild localized infections of the respiratory and intestinal tract. However, highly pathogenic influenza A strains, such as H5N1, cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. There are currently 18 different influenza A virus HA antigenic subtypes (H1 to H18) and 11 different influenza A virus NA antigenic subtypes (N1 to N11). H1-H16 and N1-N9 are found in wild bird hosts and may be a pandemic threat to humans. H17-H18 and N10-N11 have been described in bat hosts and are not currently thought to be a pandemic threat to humans.

Specific examples of influenza A include, but are not limited to: H1N1 (such as 1918 H1N1), H1N2, H1N7, H2N2 (such as 1957 H2N2), H2N1, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6, and H14N5. In one example, influenza A includes those that circulate in humans such as H1N1, H1N2 and H3N2, or cause zoonotic infections, such as H7N9 and H5N1.

In animals, most influenza A viruses cause self-limited localized infections of the respiratory tract in mammals and/or the intestinal tract in birds. However, highly pathogenic influenza A strains, such as H5N1, cause systemic infections in poultry in which mortality may reach 100%. In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Influenza B virus (IBV): A negative-sense, single-stranded, RNA virus, which has eight RNA segments. The capsid of IBV is enveloped while its virion includes an envelope, matrix protein, nucleoprotein complex, a nucleocapsid, and a polymerase complex. The surface projection are made of neuraminidase (NA) and hemagglutinin (HA). This virus is less prone to evolution than influenza A, but it mutates enough such that lasting immunity has not been achieved. The host range of influenza B is narrower than influenza A, and is only known to infect humans and seals.

Influenza B viruses are not divided into subtypes, but can be further broken down into lineages and strains. Specific examples of influenza B include, but are not limited to: B/Yamagata, B/Victoria, B/Shanghai/361/2002 and B/Hong Kong/330/2001.

Locked nucleic acid (LNA): A modified RNA nucleotide. The ribose moiety of an LNA nucleotide is modified with an extra bridge connecting the 2' oxygen and the 4' carbon.

Morpholino oligonucleotides: A type of antisense oligonucleotide. Morpholino oligonucleotides have standard nucleic acid bases, but the bases are bound to morpholino rings instead of deoxyribose rings, and are linked through phosphorodiamidate groups instead of phosphates. Replacement of anionic phosphates with the uncharged phosphorodiamidate groups eliminates ionization in the usual physiological pH range, thus morpholinos in organisms or cells are uncharged molecules. Unlike many other types of antisense compounds, morpholino oligonucleotides do not promote degradation of target mRNAs, but rather act by steric blocking. The structure and preparation of morpholino oligonucleotides is detailed in U.S. Pat. Nos. 5,698,685, 5,217,866, 5,142,047, 5,034,506, 5,166,315, 5,185,444, 5,521,063, and 5,506,337, and U.S. Patent Application Publication No. 2009/0171075, each of which is herein incorporated by reference.

Parenteral administration: Administration outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some embodiments, the pharmaceutically acceptable carrier is suitable for delivery to an airway. Carriers for airway delivery are well known in the art and are discussed below.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular vertebrate organisms, a category that includes both human and veterinary subjects, including human and non-human mammals (including research subjects such as mice).

Synthetic: Produced by artificial means in a laboratory, for example a synthetic oligonucleotide can be chemically synthesized in a laboratory.

Therapeutically effective amount: A quantity of a specified pharmaceutical or therapeutic agent sufficient to achieve a desired effect in a subject, or in a cell, being treated with the pharmaceutical or therapeutic agent. For example, this can be the amount of an ASO to treat and/or alleviate one or more symptoms of an influenza virus infection. The effective amount of the pharmaceutical agent will be dependent on several factors, including, but not limited to, the subject being treated, the severity of the condition (such as viral infection), the stage of infection, and the manner of administration of the therapeutic composition.

Unless otherwise explained, all technical and scientific terms used herein have the same meaning as commonly understood by one of ordinary skill in the art to which this disclosure belongs. The singular terms “a,” “an,” and “the” include plural referents unless context clearly indicates otherwise. “Comprising A or B” means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Described herein are ASOs that bind to conserved regions of the influenza A virus genome that are involved in RNA-NP interactions required for virus packaging. The ASOs inhibit virus replication and can be used as a treatment for influenza A virus infection.

Provided herein are compositions that include a pharmaceutically acceptable carrier and at least one antisense oligonucleotide (ASO) selected from an ASO having at least 90%, at least 95%, at least 96%, at least 97%, at least 98% or at least 99% sequence identity with SEQ ID NO: 1; an ASO having at least 90%, at least 95%, at least 96%, at least 97%, at least 98% or at least 99% sequence identity with SEQ ID NO: 2; an ASO having at least 90%, at least 95%, at least 96%, at least 97%, at least 98% or at least 99% sequence identity with SEQ ID NO: 3; an ASO having at least 90%, at least 95%, at least 96%, at least 97%, at least 98% or at least 99% sequence identity with SEQ ID NO: 4; an ASO having at least 90%, at least 95%, at least 96%, at least 97%, at least 98% or at least 99% sequence identity with SEQ ID NO: 5; and an ASO having at least 90%, at least 95%, at least 96%, at least 97%, at least 98% or at least 99% sequence identity with SEQ ID NO: 6.

In some embodiments, the at least one ASO is selected from: an ASO no more than 55, no more than 54, no more than 53, no more than 52, or no more than 51 nucleotides in length and having at least 90% sequence identity with SEQ ID NO: 1; an ASO no more than 40, no more than 39, no more than 38, or no more than 37 nucleotides in length having at least 90% sequence identity with SEQ ID NO: 2; an ASO no more than 43, no more than 42, no more than 41, or no more than 40 nucleotides in length and having at least 90% sequence identity with SEQ ID NO: 3; an ASO no more than 42, no more than 41, no more than 40 or no more than 39 nucleotides in length and having at least 90% sequence identity with SEQ ID NO: 4; an ASO no more than 46, no more than 45, no more than 44, or no more than 43 nucleotides in length and having at least 90% sequence identity with SEQ ID NO: 5; and an ASO no more than 38, no more than 37, or no more than 36 nucleotides in length and having at least 90% sequence identity with SEQ ID NO: 6.

In some embodiments, the at least one ASO is selected from: an ASO no more than 52, or no more than 51 nucleotides in length and having at least 95% sequence identity with SEQ ID NO: 1; an ASO no more than 37 nucleotides in length having at least 95% sequence identity with SEQ ID NO: 2; an ASO no more than 41, or no more than 40 nucleotides in length having at least 95% sequence identity with SEQ ID NO: 3; an ASO no more than 40, or no more than 39 nucleotides in length having at least 95% sequence identity with SEQ ID NO: 4; an ASO no more than 44, or no more than 43 nucleotides in length having at least 95% sequence identity with SEQ ID NO: 5; and an ASO no more than 36 nucleotides in length having at least 95% sequence identity with SEQ ID NO: 6.

In some embodiments, the at least one ASO is selected from: an ASO no more than 55, no more than 54, no more than 53, no more than 52, or no more than 51 nucleotides in length comprising SEQ ID NO: 1; an ASO no more than 40, no more than 39, no more than 38, or no more than 37 nucleotides in length comprising SEQ ID NO: 2; an ASO no more than 43, no more than 42, no more than 41, or no more than 40 nucleotides in length comprising SEQ ID NO: 3; an ASO no more than 42, no more than 41, no more than 40, or no more than 39 nucleotides in length comprising SEQ ID NO: 4; an ASO no more than 46, no more than 45, no more than 44, or no more than 43 nucleotides in length and comprising SEQ ID NO: 5; and an ASO no more than 38, no more than 37, or no more than 36 nucleotides in length comprising SEQ ID NO: 6.

In some embodiments, the at least one ASO is selected from: an ASO having a nucleotide sequence consisting of SEQ ID NO: 1; an ASO having a nucleotide sequence consisting of SEQ ID NO: 1; an ASO having a nucleotide sequence consisting of SEQ ID NO: 3; an ASO having a nucleotide sequence consisting of SEQ ID NO: 4; an ASO having a nucleotide sequence consisting of SEQ ID NO: 5; and an ASO having a nucleotide sequence consisting of SEQ ID NO: 6.

Also provided herein are compositions that include a pharmaceutically acceptable carrier and at least one ASO selected from an ASO comprising at least 20, at least 25 or at least 30 consecutive nucleotides of SEQ ID NO: 1; an ASO comprising at least 20, at least 25 or at least 30 consecutive nucleotides of SEQ ID NO: 2; an ASO comprising at least 20, at least 25 or at least 30 consecutive nucleotides of SEQ ID NO: 3; an ASO comprising at least 20, at least 25 or at least 30 consecutive nucleotides of SEQ ID NO: 4; an ASO comprising at least 20, at least 25 or at least 30 consecutive nucleotides of SEQ ID NO: 5; or an ASO comprising at least 20, at least 25 or at least 30 consecutive nucleotides of SEQ ID NO: 6. In some embodiments, the at least one ASO is 20, 21, 22, 23, 24, 25, 26, 27, 28, 29 or 30 consecutive nucleotides of SEQ ID NO: 1, SEQ ID NO: 2, SEQ ID NO: 3, SEQ ID NO: 4, SEQ ID NO: 5 and/or SEQ ID NO: 6. In particular examples, the at least one ASO is 25 consecutive nucleotides of SEQ ID NO: 1, SEQ ID NO: 2, SEQ ID NO: 3, SEQ ID NO: 4, SEQ ID NO: 5 and/or SEQ ID NO: 6.

In some examples, the composition includes at least 2, at least 3, at least 4 or at least 5 of the ASOs. In specific examples, the composition includes all six of the ASOs.

In some embodiments, the at least one ASO comprises at least one modification that increases nuclease resistance and/or increases binding affinity. In some examples, the at least one ASO comprises at least one phosphorothioate, at least one 2'-fluoro, at least one 2'-O-methyl, at least one 2'-O-methoxy-ethyl, at least one morpholino and/or at least one locked nucleic acid (LNA).

In some embodiments, the at least one ASO is formulated for oral, inhalation or parenteral administration.

Also provided herein are ASOs having at least 90%, at least 95%, at least 96%, at least 97%, at least 98% or at least 99% sequence identity to SEQ ID NO: 1, SEQ ID NO: 2, SEQ ID NO: 3, SEQ ID NO: 4, SEQ ID NO: 5 or SEQ ID NO: 6. In some embodiments, the ASOs comprise or consist of SEQ ID NO: 1, SEQ ID NO: 2, SEQ ID NO: 3, SEQ ID NO: 4, SEQ ID NO: 5 or SEQ ID NO: 6.

In some examples, the ASO is no more than 55, no more than 54, no more than 53, no more than 52, or no more than 51 nucleotides in length and is at least 90%, at least 95%, at least 96%, at least 97%, at least 98% or at least 99% sequence identity to SEQ ID NO: 1.

In some examples, the ASO is no more than 40, no more than 39, no more than 38, or no more than 37 nucleotides in length and is at least 90%, at least 95%, at least 96%, at least 97%, at least 98% or at least 99% sequence identity to SEQ ID NO: 2.

In some examples, the ASO is no more than 43, no more than 42, no more than 42, or no more than 40 nucleotides in length and is at least 90%, at least 95%, at least 96%, at least 97%, at least 98% or at least 99% sequence identity to SEQ ID NO: 3.

In some examples, the ASO is no more than 42, no more than 41, no more than 40, or no more than 39 nucleotide in length and is at least 90%, at least 95%, at least 96%, at least 97%, at least 98% or at least 99% sequence identity to SEQ ID NO: 4.

In some examples, the ASO is no more than 46, no more than 45, no more than 44, or no more than 43 nucleotides in length and is at least 90%, at least 95%, at least 96%, at least 97%, at least 98% or at least 99% sequence identity to SEQ ID NO: 5.

In some examples, the ASO is no more than 38, no more than 37, or no more than 36 nucleotides in length and is at least 90%, at least 95%, at least 96%, at least 97%, at least 98% or at least 99% sequence identity to SEQ ID NO: 6.

In some embodiments, the ASO comprises at least one modification that increases nuclease resistance and/or increases binding affinity. In some examples, the at least one ASO comprises at least one phosphorothioate, at least one 2'-fluoro, at least one 2'-O-methyl, at least one 2'-O-methoxy-ethyl, at least one morpholino and/or at least one locked nucleic acid (LNA).

In some embodiments, the ASO is formulated for oral, inhalation or parenteral administration.

Further provided herein are methods of inhibiting replication of an influenza A virus in a host cell by contacting the cell with a composition or ASO disclosed herein. In some embodiments, the method is an in vitro method. In other embodiments, the method is an in vivo method wherein contacting the cell comprises administering the composition to a subject infected with an influenza A virus. In some examples of the in vivo method, the method further includes administering to the subject a second influenza antiviral therapeutic agent. In particular examples, the influenza antiviral therapeutic agent comprises oseltamivir, zanamivir, peramivir, amantadine or rimantadine. In some examples, the composition or ASO is administered by oral, inhalation or parenteral administration.

Also provided are methods of treating an influenza A virus infection in a subject by administering to the subject a composition or ASO disclosed herein. In some embodiments, the method further includes administering to the subject a second influenza antiviral therapeutic agent. In particular examples, the influenza antiviral therapeutic agent comprises oseltamivir, zanamivir, peramivir, amantadine or rimantadine. In some examples, the composition or ASO is administered by oral, inhalation or parenteral administration.

IV. Antisense Oligonucleotide Modifications

In some embodiments, the antisense oligonucleotides described herein contain one or more modifications to enhance nuclease resistance and/or to increase binding affinity of the ASO to its target RNA. Modified antisense oligonucleotides include those comprising modified backbones (such as those having non-natural internucleoside linkages), modified sugar moieties or modified bases.

In some embodiments herein, the ASO includes at least one chemical modification that increases its resistance to nucleases. In specific examples, the ASO includes as least one of the following modifications: phosphorothioate, 2'-fluoro, 2'-O-methyl, 2'-O-allyl, 2'-O-propyl, 2'-O-pentyl, 2'-O-alkyl, 2'-O-aminopropyl, 2'-O-methoxy-ethyl (MOE), morpholino, phosphoramidite, α-nucleoside, methylphosphonate, LNA, S-constrained-ethyl (cEt), triyclo-DNA (tc-DNA) or peptide nucleic acid (PNA) (see Evers et al., *Adv Drug Deliv Rev* 87:90-103, 2015 for a review of chemical modifications for therapeutic ASOs).

In some embodiments herein, the ASO includes at least one chemical modification that increases its affinity for target RNA. In specific examples, the ASO includes at least one of the following modifications: phosphoramidate, LNA, 2'-O-methyl, 2'-MOE, 2'-fluoro, cEt, tc-DNA, morpholino or PNA.

Antisense oligonucleotides having modified backbones include those that retain a phosphorus atom in the backbone and those that do not have a phosphorus atom in the backbone. Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In some embodiments, both the sugar and the internucleoside linkage of the nucleotide units of the antisense oligonucleotide are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, which are herein incorporated by reference. Further teaching of PNA compounds can be found in Nielsen et al. (*Science* 254, 1497-1500, 1991).

Modified antisense oligonucleotides can also contain one or more substituted sugar moieties. In some examples, the antisense oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv Chim Acta* 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense oligonucleotides can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Antisense oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808, incorporated by reference; and Sanghvi, Y. S., Chapter 15, Antisense Research and Applications, pages 289-302, Crooke, S. T. and Lebleu, B., ed., CRC Press, 1993). Certain of these modified bases are useful for increasing the binding affinity of antisense oligonucleotides. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

V. Administration of Antisense Oligonucleotides

Antisense oligonucleotides can be delivered to a cell, tissue or organ using any of a number of methods well known in the art. Methods of administration include, but are not limited to, intradermal, intramuscular, intraperitoneal, parenteral, intravenous, subcutaneous, vaginal, rectal, intranasal, inhalation, oral or by gene gun.

Intranasal administration refers to delivery of the compositions into the nose and nasal passages through one or both of the nares and can comprise delivery by a spraying mechanism or droplet mechanism, or through aerosolization of the ASO. Administration of the compositions by inhalant can be through the nose or mouth via delivery by spraying or droplet mechanisms. Delivery can be directly to any area of the respiratory system via intubation.

Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

ASOs can also be delivered by oral administration. In some embodiments, the ASO is conjugated to triantennary N-acetyl galactosamine (GalNAc or GN3; see Prakash et al., *Nucleic Acids Res* 42(13):8796-8807, 2014).

ASOs can also be administered to a subject and/or delivered to a cell by liposomal-mediated transfection, electroporation or conjugation of the ASO to a cell-penetrating peptide (CPP). Transfection of antisense oligonucleotides generally involves the use of liposomal-mediated transfection reagents, a number of which are commercially available. Methods for transfection and electroporation of nucleic acids, including antisense oligonucleotides, are well known in the art (see, for example, U.S. Pat. Nos. 7,307,069 and 7,288,530; Pretchtel et al., *J. Immunol. Methods* 311(1-2): 139-52, 2006; Ghartey-Tagoe et al., *Int. J. Pharm.* 315(1-2):122-133, 2006).

CPPs are a family of polypeptides that facilitate transduction of proteins, nucleic acids or other compounds across membranes in a receptor-independent manner (Wadia and Dowdy, *Curr. Protein Pept. Sci.* 4(2):97-104, 2003). Typically, CPPs are short polycationic sequences that can facilitate cellular uptake of compounds to which they are linked into endosomes of cells. For example, delivery of antisense compounds by covalently-linked cationic cell penetrating peptides has been previously described (Abes et al., *J. Control Release* 116(3):304-13, 2006).

Antisense oligonucleotides are administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Compositions for oral administration may include powders or granules, suspensions or solutions in water or non-aqueous media, capsules, sachets, or tablets. Thickeners, flavorings, diluents, emulsifiers, dispersing aids or binders may be desirable.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Administration can be accomplished by single or multiple doses. The dose required will vary from subject to subject depending on the species, age, weight and general condition of the subject, the particular antisense oligonucleotides being used and its mode of administration. An appropriate dose can be determined by one of ordinary skill in the art using only routine experimentation. If administered in multiple doses, the time between delivery of each dose can vary between days, weeks, months and years.

Antisense oligonucleotides may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense oligonucleotides can also be modified to have one or more stabilizing groups that are generally attached to one or both termini of antisense oligonucleotides to enhance properties such as, for example, nuclease stability. Included in stabilizing groups are cap structures. These terminal modifications protect the antisense oligonucleotide having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense oligonucleotide to impart nuclease stability include those disclosed in WO 03/004602, which is herein incorporated by reference.

The following examples are provided to illustrate certain particular features and/or embodiments. These examples should not be construed to limit the disclosure to the particular features or embodiments described.

EXAMPLES

Example 1: Materials and Methods

This example describes the experimental procedures and materials used for the studies described in Example 2.

Cells and Viruses

MDCK cells were cultured in Eagle's Minimum Essential Medium (EMEM) supplemented with 10% FBS, L-glutamine and penicillin/streptomycin at 37° C. in a 5% $CO_2$ atmosphere. Rescue of recombinant A/WSN/1933 (H1N1) and A/California/07/2009 (H1N1) strains were previously described (Lakdawala et al., *PLoS Pathog* 10(3):e1003971, 2014; Lakdawala et al., *Virology* 446(1-2):349-356, 2013). A/Panama/07/1999 (H3N2) virus was obtained through the WHO Global Influenza Surveillance Response System. B/Texas/02/2013 was obtained from the International Reagent Resource (IRR, formerly known as Influenza Reagents Resource).

HITS-CLIP and Deep Sequencing Data Analysis

Two confluent T175 flasks of MDCK cells were washed twice with phosphate-buffered saline (PBS) and infected at a dilution of 1:10,000 with the indicated virus in serum-free EMEM containing TCPK-trypsin (Worthington Biochemicals). At 96 hours post-infection, the culture medium was harvested and cellular debris was pelleted by centrifugation at 2,000×g for 20 minutes. UV crosslinking (400 mJ/cm² followed by 200 mJ/cm²) was performed on clarified culture medium. Crosslinked virus supernatant was layered onto a 30% sucrose-NTE (100 mM NaCl, 10 mM Tris pH7.4, 1 mM EDTA) cushion and centrifuged at 200,000×g for 2 hours at 4° C. HITS-CLIP was carried out as previously described with minor modifications (Moore et al., Nat Protoc 9(2):263-293, 2014). Briefly, virus particles concentrated from 25 mL of culture supernatant were resuspended in 300 µl PXL buffer (PBS, 1% NP40, 0.5% deoxycholate, 0.1% SDS), followed by DNase and RNase treatment. For each viral strain sample, partial RNase digestions were carried out for 5 minutes at 37° C. with three aliquots of 100 µl viral lysate and a ten-fold dilution series of RNase A (0.25 µg, 0.025 µg, and 0.0025 µg total amount of enzyme, respectively). The following antibodies were used for immunoprecipitating influenza NPs of different strains: mouse monoclonal HB65 antibody for A/WSN/33; mouse monoclonal antibody MAB8251 (Millipore) for H1N1pdm (A/CA/07/2009) and A/Panama/07/1999; mouse monoclonal antibody ab2074 (Abcam) for B/Texas/02/2013. For each IP reaction, 25 µl of antibody-Dynabeads Protein G complexes were used. Ligation of 5' and 3' adapters, RT reaction and first PCR amplification step were carried out as described (Moore et al., Nat Protoc 9(2):263-293, 2014). The first round PCR products were then converted into an Illumina-compatible deep sequencing library using the NEBNext Ultra DNA Library Prep kit (NEB), and deep sequencing was carried out using Illumina's NextSeq platform. Data analysis was performed as described (Moore et al., Nat Protoc 9(2):263-293, 2014) using the Novolign alignment program and mapping the reads to reference genomes available from the NCBI database. Sequencing results were displayed on Integrated Genome Viewer (Thorvaldsdottir et al., Brief Bioinform 14(2):178-192, 2013). Table 1 lists the total read number, number of mapped reads, and the SRA accession number for each sample.

TABLE 1

SRA Accession numbers

| | Strain | Total Reads | Reads Mapped | SRA Accession No |
|---|---|---|---|---|
| HITS-CLIP | WSN Rep 1 | 757054 | 96799 | SRR4449824 |
| | WSN Rep 2 | 1087662 | 291130 | SRR4449827 |
| | H1N1pdm | 2083612 | 195984 | SRR4449821 |
| | H3N2 | 12931353 | 1656213 | SRR4449823 |
| | IBV | 2120239 | 362579 | SRR4449828 |
| RNA Input | WSN | 2204195 | 363763 | SRR4449825 |
| | H1N1pdm | 2083612 | 195984 | SRR4449826 |
| | H3N2 | 1176421 | 665217 | SRR4449820 |
| | IBV | 84940 | 20004 | SRR4449822 |

For deep sequencing total RNA from virions ('input' samples), first and second cDNA strands were synthesized using NEBNext mRNA Library Prep kit (New England Biologicals). Double-stranded cDNAs were then converted into deep sequencing libraries using Illumina's Nextera XT DNA Library Prep Kit. Deep sequencing data were deposited in the Sequence Read Archive under accession numbers SRR4449820-8.

Pearson Correlation Analysis

HITS-CLIP RNAseq data were normalized to the highest peak per segment (excluding super peaks). The normalized read depth at each nucleotide position was compared between H1N1, H3N2, and IBV strains using the Prism 6 software (Bitplane). The Pearson values and corresponding p-values determined between influenza virus strains for each segment are presented in Table 2. In general, Pearson values (r) range from 1 to −1, where r≥0.7 demonstrates a high positive correlation, 0.5≤r<0.7 is a moderate positive correlation, 0.3≤r<0.5 is low positive correlation, and r<0.3 is a negligible correlation (Mukaka, Malawi Med J 24(3):69-71, 2012). Statistical p-values are difficult to determine on pairs of samples with negligible correlation, which explains the p-values >0.01 for Pearson correlations of IAV and IBV.

Peak Calling Using Model-Based Analysis for ChIP-Seq (MACS)

The peak-finding algorithm MACS was used to predict NP binding sites (Zhang et al., Genome Biol 9(9):R137, 2008). For each HITS-CLIP experiment, a p-score was chosen that exhibited the best performance in terms of calling NP peaks. Non-peaks were defined as regions longer than 25 nucleotides that had a HITS-CLIP read coverage of less than 5% of the maximum peak height of each experiment. Mean peak widths were calculated using the coordinates obtained from MACS analysis, omitting apparent double peaks that were called as a single peak by the algorithm.

vRNA Accessibility Assay

Virions from 25 ml culture supernatant were harvested by ultracentrifugation (see above) and resuspended in 100 µl Digestion buffer (50 mM HEPES pH 7.5, 75 mM NaCl, 3 mM $MgCl_2$, 10 mM DTT, 1% NP-40 and 0.05% Triton X-100). Viral lysate was then diluted five-fold in Digestion buffer containing no Triton X-100. To examine accessibility of vRNA regions, DNA antisense oligonucleotides (ASOs) complementary to segment 5 (NP) of A/WSN/33 (positions shown in FIG. 1B) and RNase H were added to the lysate. For each reaction, 100 µl lysate was incubated with 5 µM ASO and 5 units RNase H for 15 minutes at 37° C. The following ASOs were used: 5'-ctcatgctctaccgact-gagctagccgggc-3' (negative control; SEQ ID NO: 7); 5'-ccttgaactgagaagcagatact-3' (ASO #1; SEQ ID NO: 8); 5'-tgtatggatctgccgtagccagtg-3' (ASO #2; SEQ ID NO: 9); 5'-tttgaatgatgcaacttaccagag-3' (ASO #3; SEQ ID NO: 10); and 5'-aggaataaatatctagaagaacat-3' (ASO #4; SEQ ID NO: 11). Following digestion, RNA was purified using TRIZOL™, resolved on a formaldehyde-containing 1% agarose gel, and transferred onto a nylon membrane for Northern blot analysis. Probes for NP and PB2 vRNAs were generated by random priming linearized pHW2000-NP and pHW2000-PB2 plasmids, respectively.

Nucleotide Variability Analysis

The variability of HA and NA was determined from 385 and 353 H1N1 sequences, respectively, spanning 1918-2010. To prevent bias from only recent strains, an attempt was made to analyze sequences spanning the last 90 years with similar distribution from older strains and the last 6 years were excluded, since little variation has been observed in the H1N1 strains circulating after emergence of the 2009 H1N1 pandemic. The precise breakdown was 193 or 149 strains from 1918-1994, 61 or 79 strains from 1.995-2005, and 131 or 125 strains from 2006-2010 for HA or NA, respectively. Sequences were obtained from GISAID (online at platform.gisaid.org) and FluDB (online at fludb.org). An overlapping 50-nucleotide sliding window analysis of nucleotide variability was performed as described (Colson, *BMC Microbiol* 6:21, 2006; Proutski, *Bioinformatics* 14(5): 467-468, 1998).

Example 2: Genome-Wide Analysis of Influenza Viral RNA and Nucleoprotein Association The studies described below were designed to define the binding profile of NP to vRNA segments using high-throughput RNA sequencing coupled with crosslinking immunoprecipitation (HITS-CLIP), which provides a sophisticated means of identifying RNA-binding sites for a RNA binding protein of interest (Licatalosi et al., *Nature* 456(7221):464-469, 2008; Ule et al., *Methods* 37(4):376-386, 2005). Using this methodology, NP association to vRNA was mapped for all eight segments of three IAV and one IBV. Contrary to all previously published schematics of vRNP structure, a distinct pattern of NP association to vRNA was observed that is neither random nor uniform for all viruses tested. It was found that IAV maintain moderately similar NP-vRNA binding profiles to each other, while there is a considerable difference between IAV and IBV strains. In addition, it was observed that vRNA nucleotide content may drive the degree of NP association. These data have substantial implications for understanding influenza virus assembly, reassortment and provide a contrast to the prevailing model of influenza vRNP structure.

Identifying NP-vRNA Association by HITS-CLIP

To map regions on vRNA that are occupied by NP, HITS-CLIP was carried out with purified virions (FIG. 1A). UV irradiation of intact virions generates covalent crosslinks between NP and directly bound vRNA to preserve the in vivo interactions. NP was then immunoprecipitated, and high-throughput sequencing was used to identify the bound vRNA regions. Three possible scenarios exist for NP association to vRNA: 1) uniform binding, as stated in the literature; 2) random but not uniform; or 3) neither random nor uniform. If the first scenario were correct, the HITS-CLIP experiment would produce uniform deep sequencing coverage across the length of the vRNA segments. In contrast, the other two scenarios would produce areas of high and low sequence coverage. HITS-CLIP was initially performed on a lab-adapted H1N1 virus, A/WSN/1933 (WSN). For each vRNA segment, multiple areas were observed that were either enriched with NP (peaks) or lacking NP protein (NP-free), defined as regions with RNAseq signal similar to background levels (FIGS. 1B and 2A). These data showing non-uniform binding of NP to vRNA are inconsistent with the prevailing model of segment packaging by NP. To ensure that the NP binding profile in virions generated by HITS-CLIP was reproducible and not random, an independent biological replicate of WSN was performed. A nearly identical NP-vRNA binding profile was observed (Pearson correlation coefficient calculated for all segments r=0.826) between the two independent biological replicates (FIG. 1B and Table 2). RNAseq of total RNA from purified virions ('input') revealed complete coverage of the RNA segments (FIG. 1B, bottom and FIG. 7) and demonstrated that the HITS-CLIP peaks are not caused by sequencing bias, as the read distribution was not mirrored in both samples (FIG. 1B, bottom). These data demonstrate that the NP-vRNA binding profiles are not random, thus ruling out scenario two. It was concluded that NP binds to vRNA in neither a uniform nor random fashion.

TABLE 2

Pearson Correlation Values of NP-vRNA Binding Profiles for All Viruses and Segments

| | | Viruses Compared In This Study | | | | | | | |
|---|---|---|---|---|---|---|---|---|---|
| | | WSN rep 2 | | CA0709 | | Panama | | Flu B | |
| | | Pearson | p-value | Pearson | p-value | Pearson | p-value | Pearson | p-value |
| Combined eight genomes | WSN rep 1 | 0.798 | 0.0000 | 0.464 | 0.0000 | 0.426 | 0.0000 | −0.054 | 0.0000 |
| | WSN rep 2 | | | 0.411 | 0.0000 | 0.306 | 0.0000 | −0.029 | 0.0006 |
| | CA0709 | | | | | 0.356 | 0.0000 | 0.018 | 0.0367 |
| | Panama | | | | | | | −0.032 | 0.0002 |
| | Flu B | | | | | | | | |
| Segment 1 (PB2) | WSN rep 1 | 0.741 | 0.0000 | 0.397 | 0.0000 | 0.252 | 0.0000 | 0.003 | 0.8894 |
| | WSN rep 2 | | | 0.399 | 0.0000 | 0.333 | 0.0000 | 0.009 | 0.6466 |
| | CA0709 | | | | | 0.206 | 0.0000 | 0.037 | 0.0747 |
| | Panama | | | | | | | 0.361 | 0.0000 |
| | Flu B | | | | | | | | |
| Segment 2 (PB1) | WSN rep 1 | 0.667 | 0.0000 | 0.397 | 0.0000 | 0.617 | 0.0000 | 0.269 | 0.0000 |
| | WSN rep 2 | | | 0.074 | 0.0004 | 0.223 | 0.0000 | 0.136 | 0.0000 |
| | CA0709 | | | | | 0.680 | 0.0000 | 0.020 | 0.3396 |
| | Panama | | | | | | | 0.166 | 0.0000 |
| | Flu B | | | | | 0.166 | 0.0000 | | |
| Segment 3 (PA) | WSN rep 1 | 0.884 | 0.0000 | 0.590 | 0.0000 | 0.752 | 0.0000 | −0.083 | 0.0001 |
| | WSN rep 2 | | | 0.663 | 0.0000 | 0.650 | 0.0000 | −0.073 | 0.0006 |
| | CA0709 | | | | | 0.676 | 0.0000 | −0.047 | 0.0254 |
| | Panama | | | | | | | −0.139 | 0.0000 |
| | Flu B | | | | | | | | |
| Segment 4 (HA) | WSN rep 1 | 0.896 | 0.0000 | 0.541 | 0.0000 | 0.272 | 0.0000 | −0.030 | 0.2087 |
| | WSN rep 2 | | | 0.685 | 0.0000 | 0.150 | 0.0000 | 0.027 | 0.2489 |
| | CA0709 | | | | | 0.146 | 0.0000 | 0.242 | 0.0000 |
| | Panama | | | | | | | 0.068 | 0.0042 |
| | Flu B | | | | | | | | |
| Segment 5 (NP) | WSN rep 1 | 0.747 | 0.0000 | 0.635 | 0.0000 | 0.425 | 0.0000 | −0.011 | 0.6372 |
| | WSN rep 2 | | | 0.390 | 0.0000 | 0.300 | 0.0000 | −0.011 | 0.6491 |
| | CA0709 | | | | | 0.345 | 0.0000 | −0.103 | 0.0000 |
| | Panama | | | | | | | 0.095 | 0.0001 |
| | Flu B | | | | | | | | |

TABLE 2-continued

Pearson Correlation Values of NP-vRNA Binding Profiles for All Viruses and Segments

| | | Viruses Compared In This Study | | | | | | |
|---|---|---|---|---|---|---|---|---|
| | | WSN rep 2 | | CA0709 | | Panama | | Flu B | |
| | | Pearson | p-value | Pearson | p-value | Pearson | p-value | Pearson | p-value |
| Segment 6 (NA) | WSN rep 1 | 0.868 | 0.0000 | 0.485 | 0.0000 | 0.432 | 0.0000 | −0.211 | 0.0000 |
| | WSN rep 2 | | | 0.538 | 0.0000 | 0.335 | 0.0000 | −0.114 | 0.0000 |
| | CA0709 | | | | | 0.367 | 0.0000 | 0.002 | 0.9362 |
| | Panama | | | | | | | −0.084 | 0.0013 |
| | Flu B | | | | | | | | |
| Segment 7 (M) | WSN rep 1 | 0.695 | 0.0000 | 0.693 | 0.0000 | 0.551 | 0.0000 | −0.271 | 0.0000 |
| | WSN rep 2 | | | 0.344 | 0.0000 | 0.702 | 0.0000 | −0.216 | 0.0000 |
| | CA0709 | | | | | 0.230 | 0.0000 | −0.216 | 0.0000 |
| | Panama | | | | | | | −0.262 | 0.0000 |
| | Flu B | | | | | | | | |
| Segment 8 (NS) | WSN rep 1 | 0.709 | 0.0000 | 0.271 | 0.0000 | 0.464 | 0.0000 | 0.302 | 0.0000 |
| | WSN rep 2 | | | 0.097 | 0.0016 | 0.430 | 0.0000 | 0.395 | 0.0000 |
| CA0709 | | | | | | 0.581 | 0.0000 | −0.186 | 0.0000 |
| Panama | | | | | | | | −0.064 | 0.0368 |
| Flu B | | | | | | | | | |

Figure 1C:
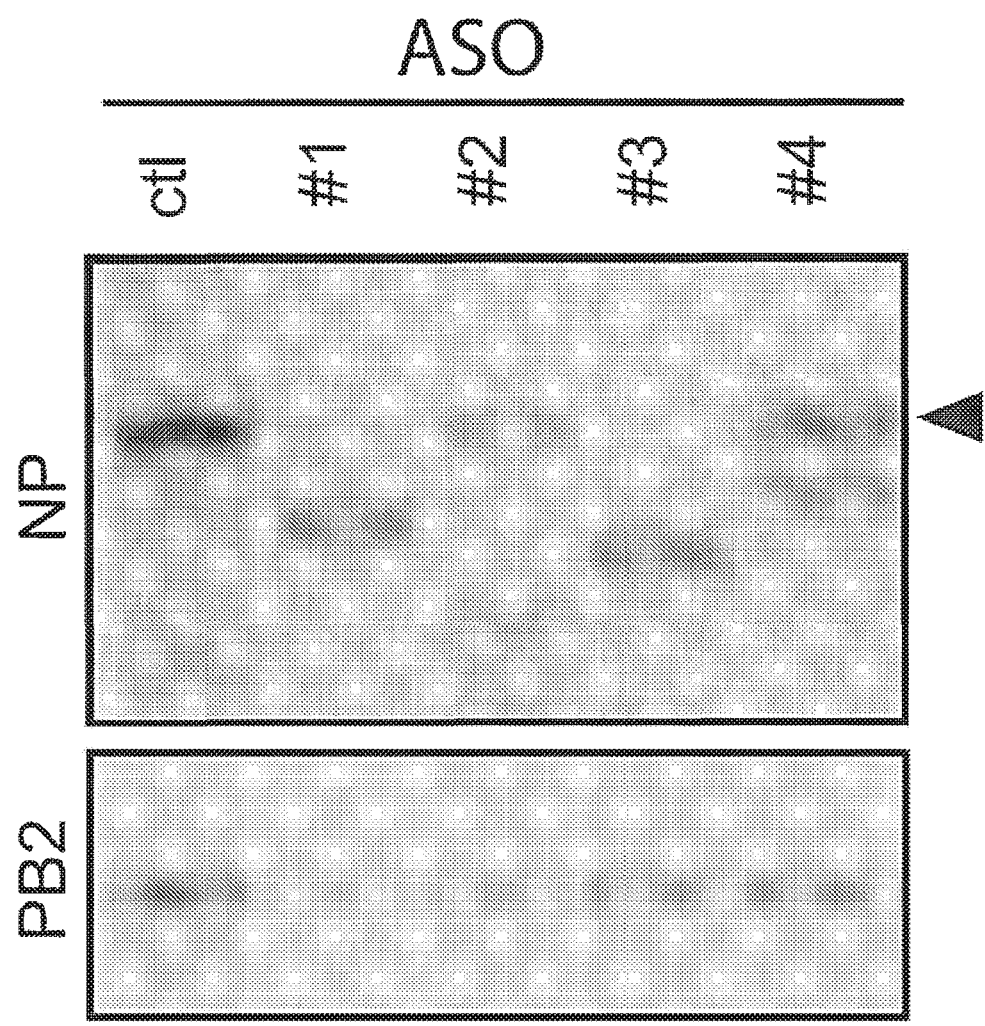

To validate the HITS-CLIP results, a study was performed to verify that the vRNA regions enriched with NP are indeed tightly associated and not accessible for hybridization. For this, DNA antisense oligonucleotides (ASO) were used that are complementary to vRNA regions that either exhibit strong NP association (peaks) or low NP bound regions (non-peaks). Accessible regions of the vRNA segment are able to base pair with ASO and in the presence of RNase H induce cleavage of the vRNA segment. In contrast, inaccessible regions due to strong NP association would not result in RNase H-mediated digestion. ASO #1 and #3 target non-peak regions, whereas ASO #2 and #4 were complementary to peaks on segment 5 (FIG. 1B). Consistent with the HITS-CLIP data, the addition of ASOs #2 and #4 inefficiently induced cleavage of segment 5 when added to viral lysate containing vRNA complexed with NP (FIG. 1C). On the other hand, ASO #1 and #3 readily formed DNA-RNA hybrids with segment 5 vRNA and induced digestion, as shown by Northern blot analysis (FIG. 1C). This result verified the NP binding profile identified by HITS-CLIP. Taken together, the absence of a regularly spaced NP binding profile and a non-random distribution clearly indicates that NP does not uniformly bind the entire length of the vRNA and that the regions of the vRNA segment with strong NP association are not capable of RNA-RNA interactions, while non-peak regions are accessible for engaging in RNA-RNA interactions.

Comparison of NP-vRNA Binding Profiles Between H1N1 Viruses

Figure 2E:
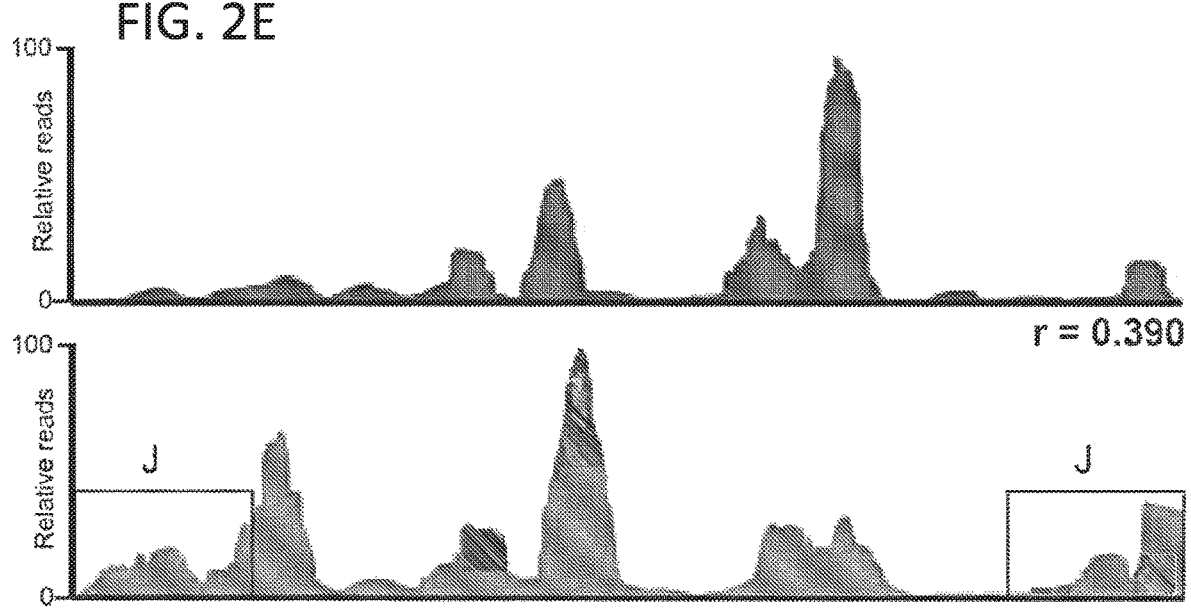
Figure 2F:
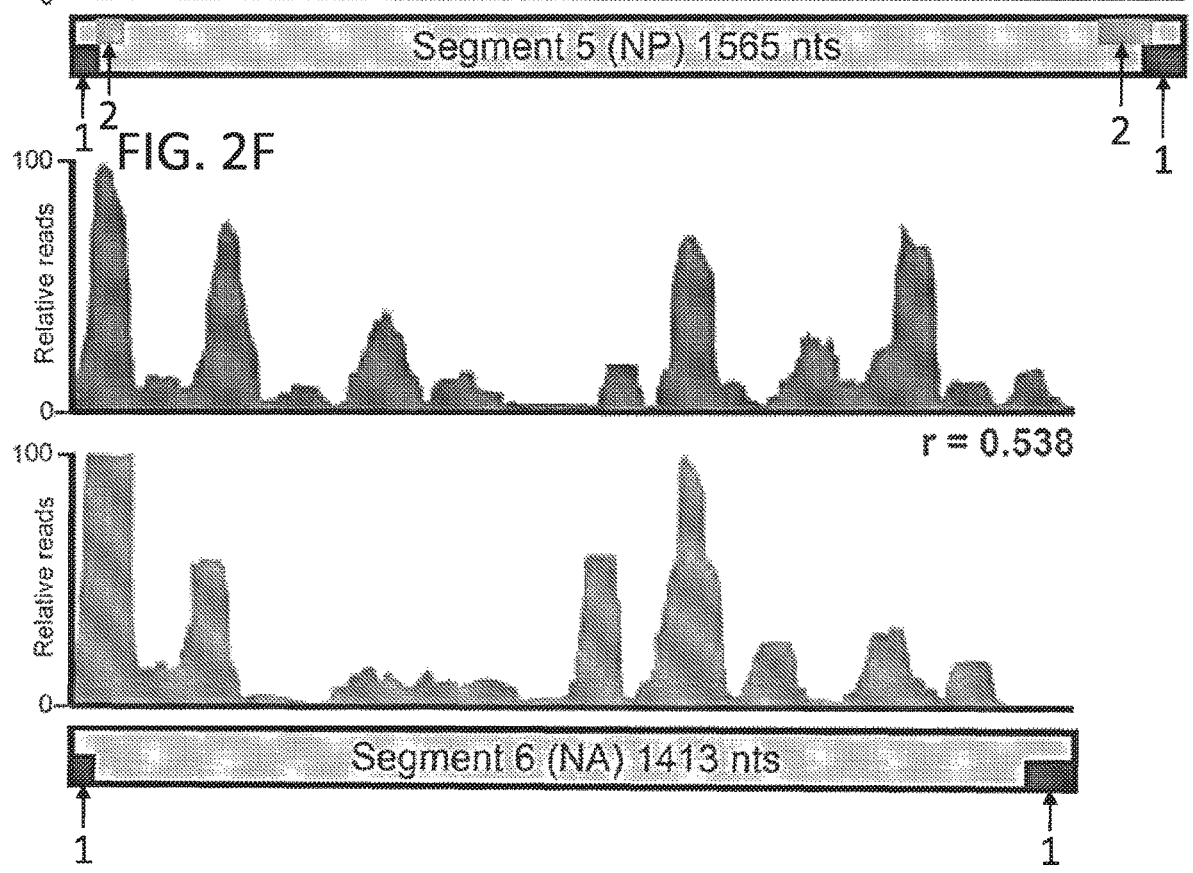

To examine the conservation of NP association between different H1N1 viruses, HITS-CLIP was performed on a 2009 H1N1pdm strain (A/California/07/2009) (FIG. 2, red). Areas of enriched NP association (peaks) and non-peak regions were observed for each segment of the H1N1pdm virus, demonstrating that NP associates in a non-random pattern to vRNA from this recent human clinical isolate similar to the lab-adapted WSN H1N1 strain. Comparing the overall NP-vRNA binding profile for all eight segments between WSN and H1N1pdm yielded a Pearson correlation coefficient of r=0.411, indicating a moderate correlation. However, the correlation of the NP-vRNA binding profile for each segment was variable between these two H1N1 strains (FIGS. 2A-2H and Table 2). It was observed that segment 3 (PA) and segment 4 (HA) were highly correlated (Pearson coefficient r=0.683 and 0.685, respectively) (FIGS. 2C and 2D), whereas segment 2 (PB1) and segment 8 (NS) displayed a very low correlation (Pearson coefficient r=0.074 and 0.097, respectively) (FIGS. 2B, 2H and Table 2). Correlation coefficients were not dependent upon the origin of the segments, since segment 2 (PB1) is derived from the human H3N2 while segments 4 (HA), 5 (NP) and 8 (NS) all originated from the classical swine lineage in the H1N1pdm virus (Neumann et al., *Nature* 459(7249):931-939, 2009). All of the Pearson correlation coefficients between WSN and H1N1pdm were statistically significant (p-value <0.001). These data suggest that H1N1 viruses share moderate in NP-vRNA binding profiles, but are not identical.

Based on previous studies demonstrating that the 5' and 3' non-coding sequences are important for packaging of vRNA, it was expected that the vRNA ends would be free of NP for promoting intersegmental interactions required for virion assembly (Eisfeld et al., *Nat Rev Microbiol* 13(1):28-41, 2015; Gerber et al., *Trends Microbiol* 22(8):446-455 2014). Unexpectedly, the packaging and bundling sequences at the 5' and 3' ends of each vRNA segment were not consistently devoid of NP binding. A few examples of vRNA segments with NP-free 5' and 3' ends were found (FIG. 2I), whereas many other segments had strong NP association at either the 5', 3' or both ends (FIG. 2J). During analysis of both input vRNA from purified virions and HITS-CLIP NP-vRNA binding profile it was ensured that the non-coding regions of each segment, based on universal 13-mers sequence (Skehel and Hay, *Nucleic Acids Res* 5(4):1207-1219, 1978) was present in each segment. Taken together, these observations suggest that the 5' and 3' ends may not be critical for RNA-RNA binding as previously proposed, or that their role in influenza assembly may be segment specific.

In order to understand the variation between WSN and H1N1pdm NP-vRNA binding profiles, the 13 positively charged amino acids that make up the NP RNA binding groove were compared (Y148, R150, R152, R156, R174, R175, K184, R195, R199, R213, R214, R221 and R236). The results showed that they were identical (Li et al., *J Virol* 83(9):4153-4162, 2009; Liu et al., *Sci Rep* 6:21662, 2016; Ye et al., *Nature* 444(7122):1078-1082, 2006; Zheng et al., *PLoS Pathog* 9(9):e1003624, 2013). Therefore, the moderate correlation between the two H1N1 viruses was not due to differences in the NP proteins.

Comparison of H3N2 and H1N1 NP-vRNA Binding Profiles

Figure 3C:
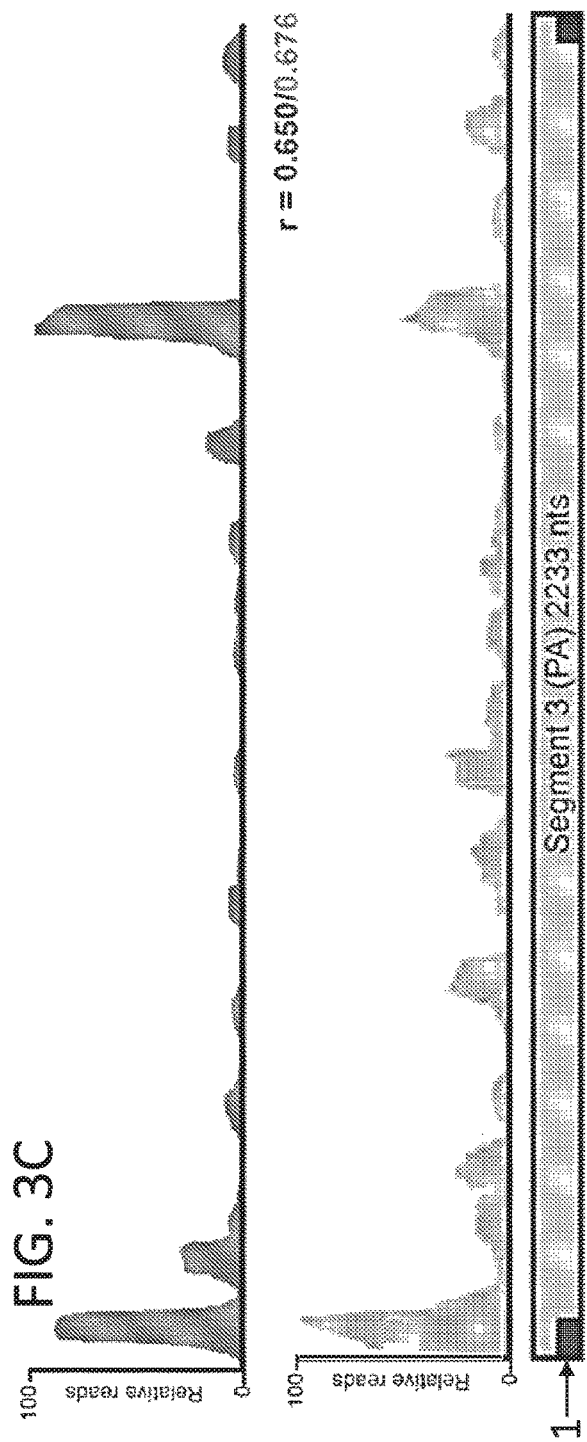
Figure 3D:
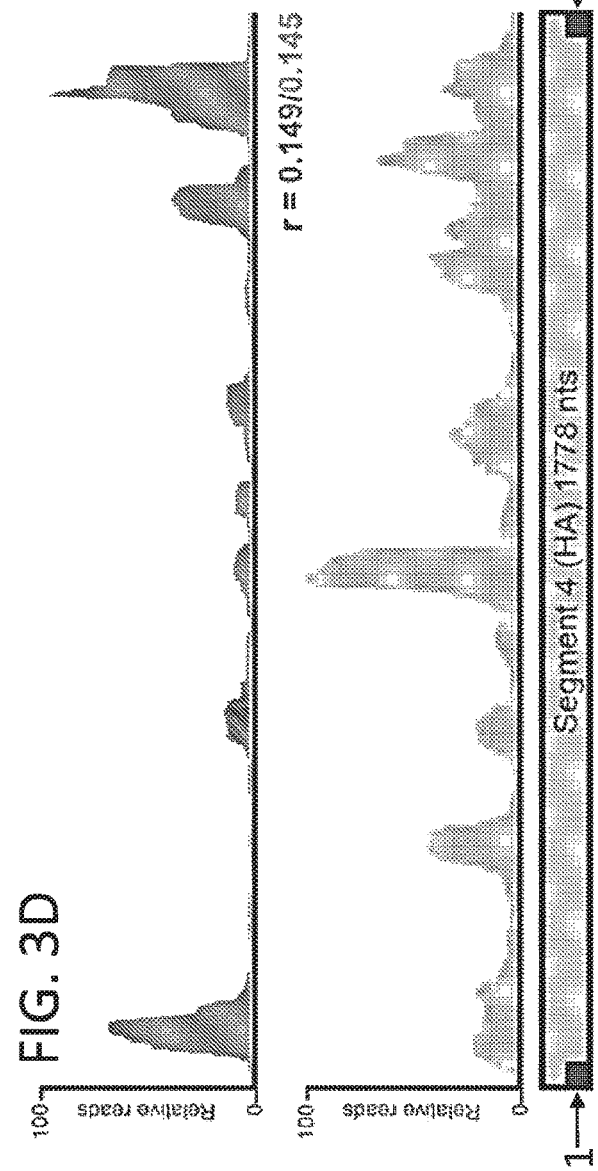
Figure 4C:
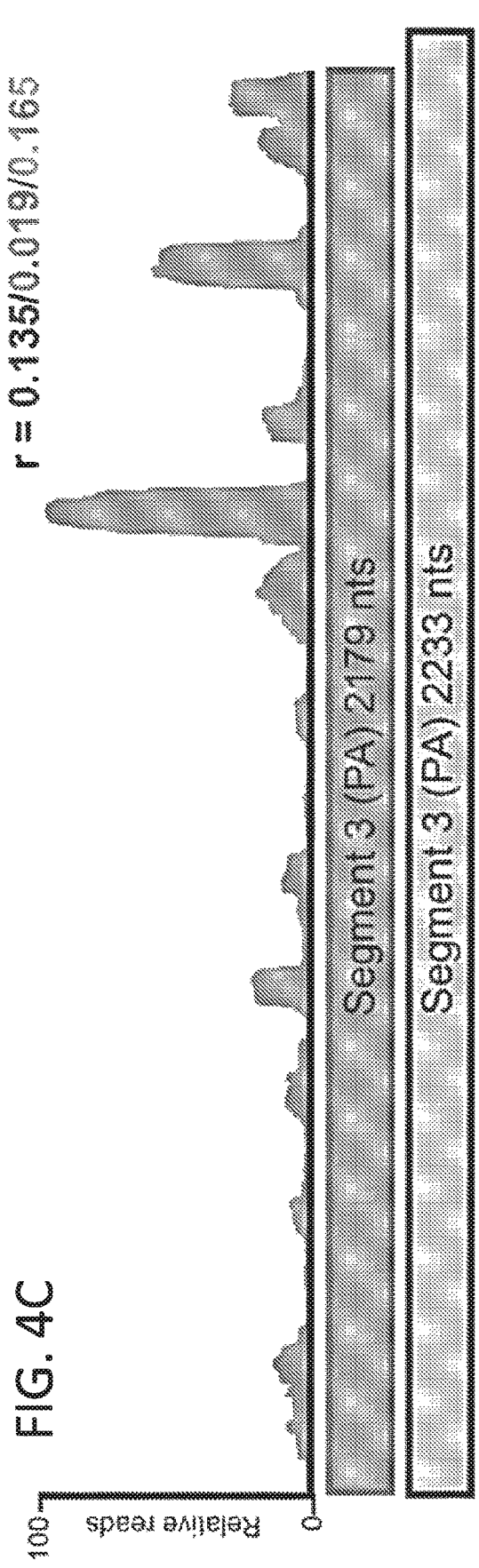
Figure 4D:
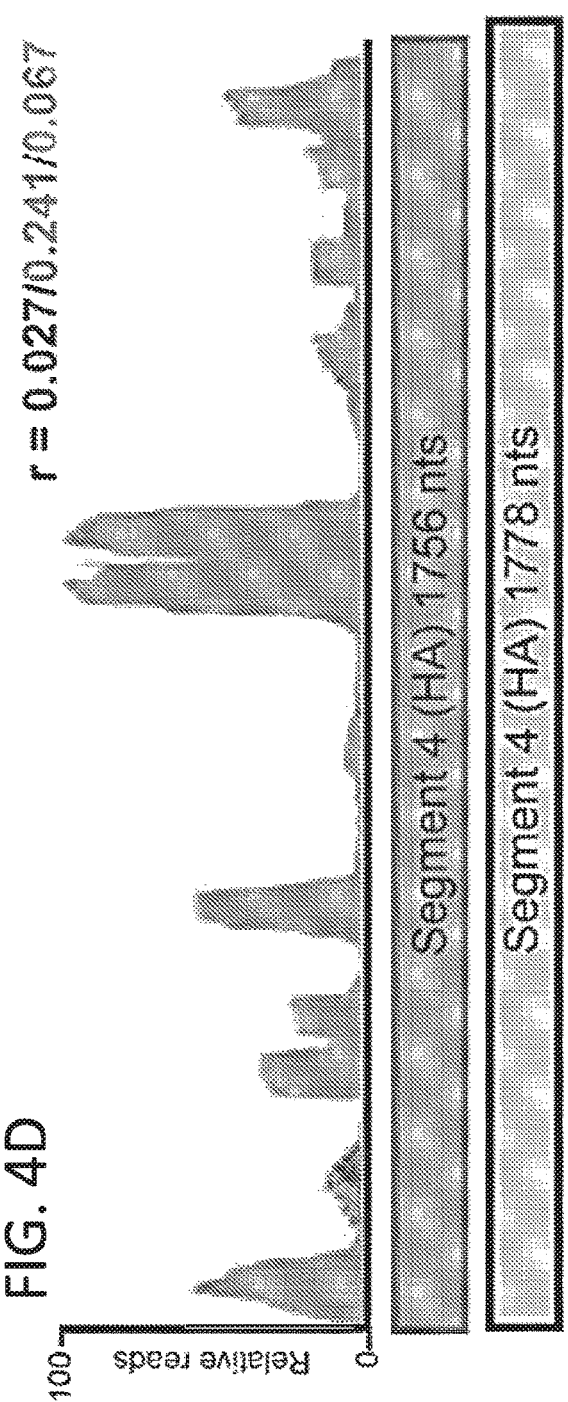
Figure 4E:
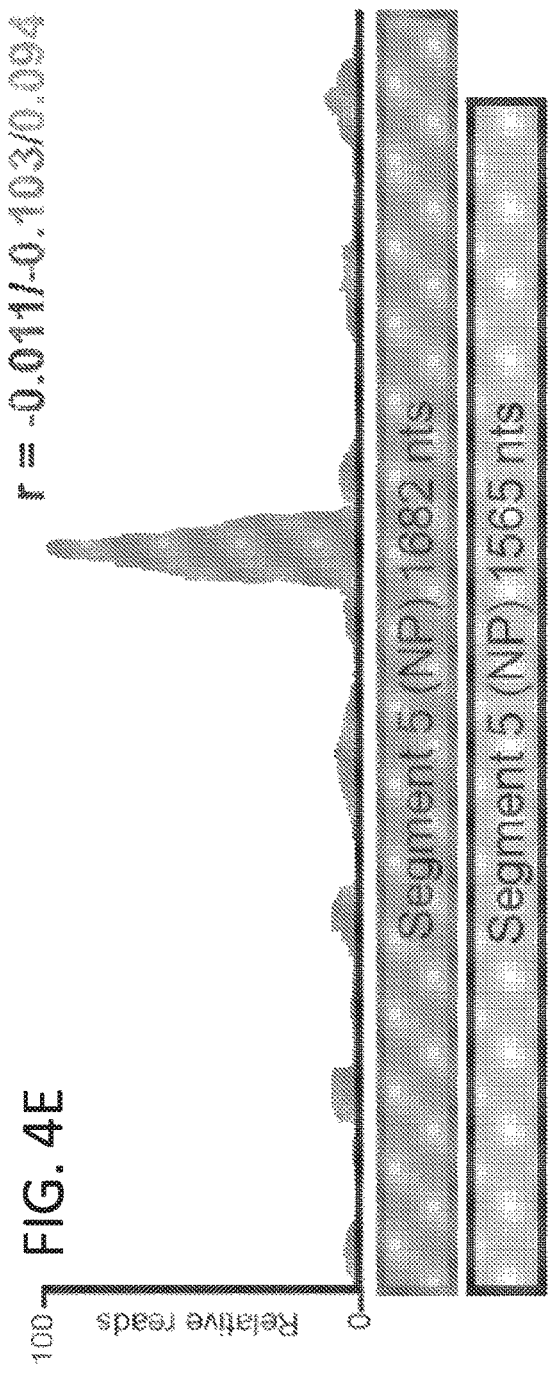
Figure 4F:
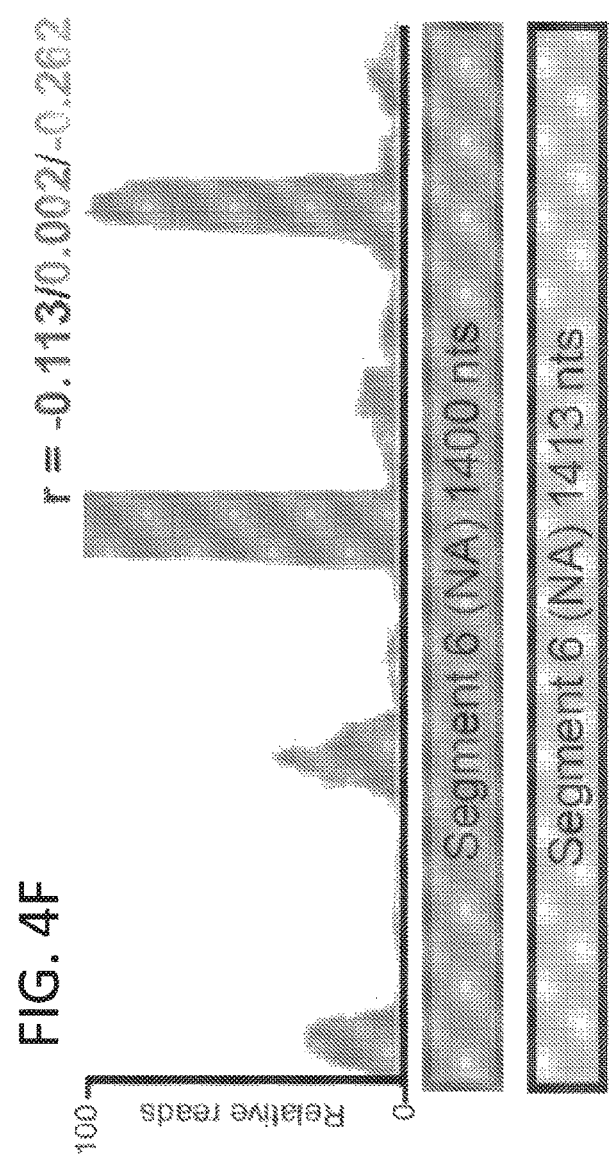
Figure 4G:
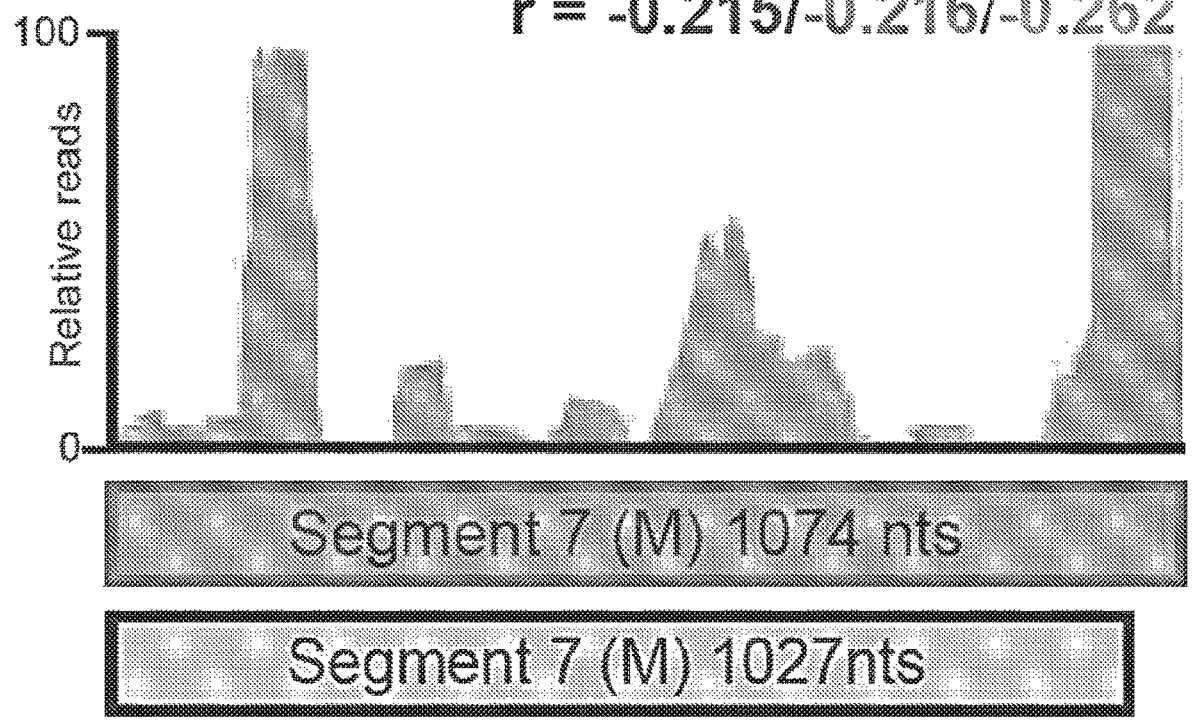
Figure 4H:
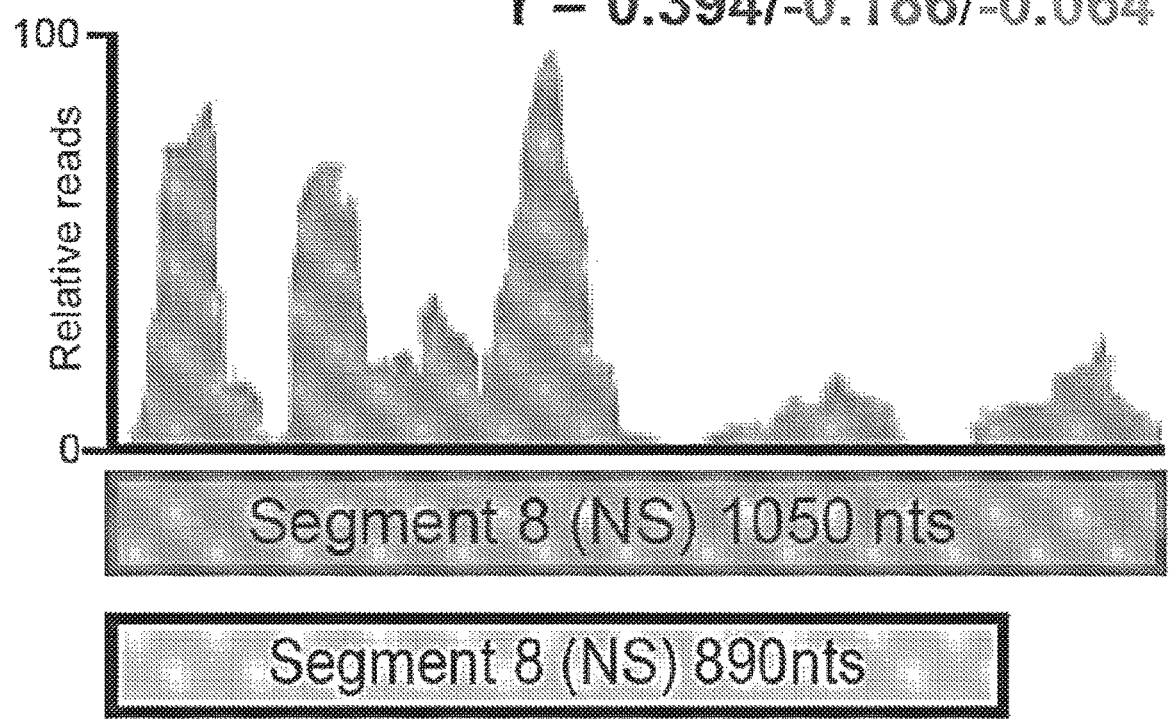

H3N2 viruses co-circulate with H1N1 viruses during seasonal epidemics in the human population and have previously reassorted to generate a novel H1N2 virus strain (Xu et al., *J Infect Dis* 186(10):1490-1493, 2002) that caused a small outbreak during the 2001-2002 season. NP HITS-CLIP was performed on a seasonal H3N2 strain from 1999 (A/Panama/07/1999) to examine its NP-vRNA association and compare it to that of H1N1 viruses. As with H1N1 viruses, the H3N2 NP associated strongly with specific regions of each vRNA segment and weakly in other regions, demonstrating preferred association of NP with certain regions (FIG. 3). A comparison of the NP binding profile of the whole genomes of WSN and H1N1pdm to H3N2 also produced moderate Pearson correlation coefficients of 0.306 and 0.356, respectively (p-value <0.001) (FIG. 4B and Table 2). Pearson correlation for each individual segment varied from low to high with segment 3 (PA) being the most highly correlated between H3N2 and H1N1 viruses (r=0.650 and 0.676, FIG. 3C), and segment 4 (HA) having the lowest Pearson correlation (r=0.150 and 0.146, FIG. 3D). The low correlation between NP-binding profiles of segment 4 (HA) is not surprising, since H1 is a group 1 hemagglutinin (HA) and H3 is a group 2 HA protein, consistent with the large genetic variation between the HA vRNA of these viruses. Interestingly, fewer non-peak regions were observed in each of the H3N2 segments with segment 2 (PB2), 7 (M) and 8 (NS) only containing one such region (FIGS. 3A, 3G and 3H, black arrowheads). Whether this indicates fewer intersegmental interactions for H3N2 viruses remains to be determined.

The IBV NP-vRNA Binding Profile Differs Considerably from IAV

Similar to IAV, IBV possess an eight-segmented genome in morphologically indistinguishable particles, but only infects humans, while IAV infect a wide-range of animal hosts (Ruigrok et al., *J Gen Virol* 65(Pt 4):799-802, 1984; Nakatsu et al., MBio 7(5), 2016). During an influenza season, in addition to H1N1 and H3N2, IBV also circulate. Despite this co-circulation, reassortment between IAV and IBV has not been observed in nature (Baker et al., *J Virol* 88(18):10778-10791, 2014). NP HITS-CLIP was performed on an IBV strain of the Victoria lineage (B/Texas/02/2013) (FIG. 4A). Similar to IAV, a profile of NP association in peaks and non-peaks was found for IBV, demonstrating that all influenza viruses have a non-random and non-uniform NP-vRNA binding profile.

Comparison of the NP-vRNA binding profile between IBV and IAV revealed Pearson correlation coefficients of all 8 segments close to 0 between IBV and WSN, H1N1pdm or H3N2 (r=−0.029, 0.018 or −0.032, respectively) (FIG. 4B and Table 2), suggesting that the NP binding pattern between IAV and IBV viruses are unrelated. However, as with IAV, some segments had higher correlation coefficients: IBV segment 8 (NS) and WSN had a coefficient of r=0.395; segment 2 (PB1) of IBV and H3N2 had a coefficient of 0.166, while displaying no sequence similarity (FIG. 4A and Table 2). The lack of correlation between IAV and IBV NP-vRNA binding profiles may help explain the absence of reassortment observed between these viruses during an influenza season.

Characterization of Enriched NP-Binding Peaks

Figure 8A:
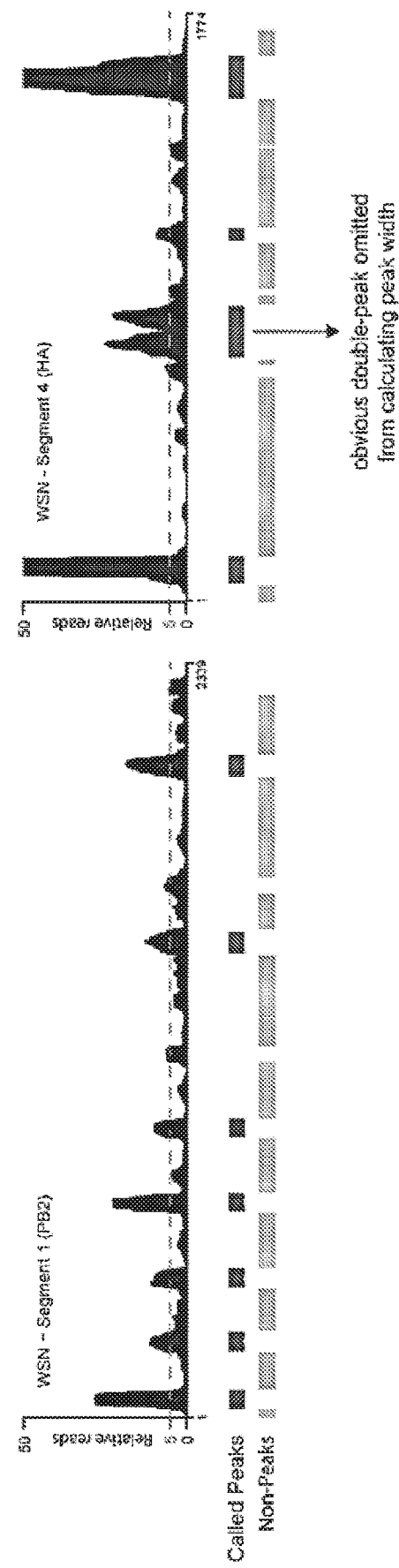
FIGS. 8A-8C: Predicted peaks by MACS and median peak width.
Figures 8B, 8C:
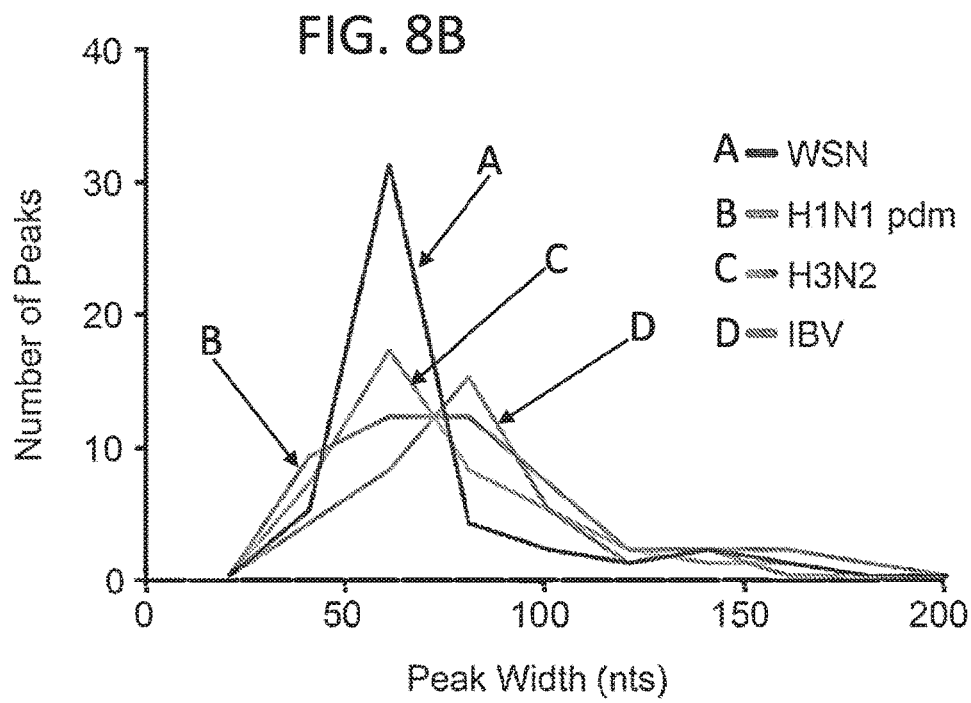

The peak-finding algorithm MACS (Model-based Analysis of ChIP-Seq) (Zhang et al., *Genome Biol* 9(9):R137, 2008) was used to predict strong NP binding sites in the HITS-CLIP data, and non-peak regions were defined as having less than 5% of the maximum peak height (FIG. 8A; see Example 1 for additional details). Analysis of peak widths for all segments of IAV and IBV indicates a narrow range of nucleotides from 63.9 to 84.8 (FIGS. 8B-8C). Given the previous observation that a single NP can associate with 20-26 nucleotides (Compans et al., *J Virol* 10(4): 795-800, 1972; Martin-Benito et al., *EMBO Rep* 2(4):313-317, 2001; Ortega et al., *J Virol* 74(1):156-163, 2000), the width of NP enriched regions suggest that a peak consists of approximately three NPs. Consistent with results herein, structural studies indicate that IAV NP are organized as trimers (Ng et al., *FASEB J* 22(10):3638-3647, 2008; Ye et al., *Nature* 444(7122):1078-1082, 2006).

Figure 5A:
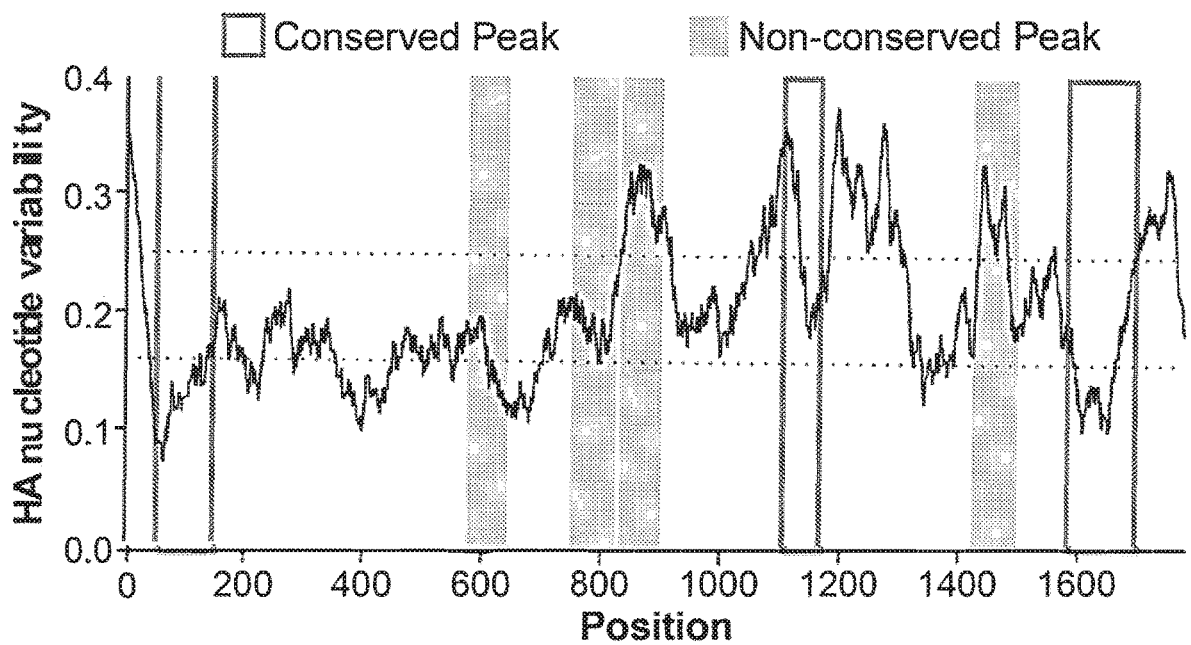
Figure 5B:
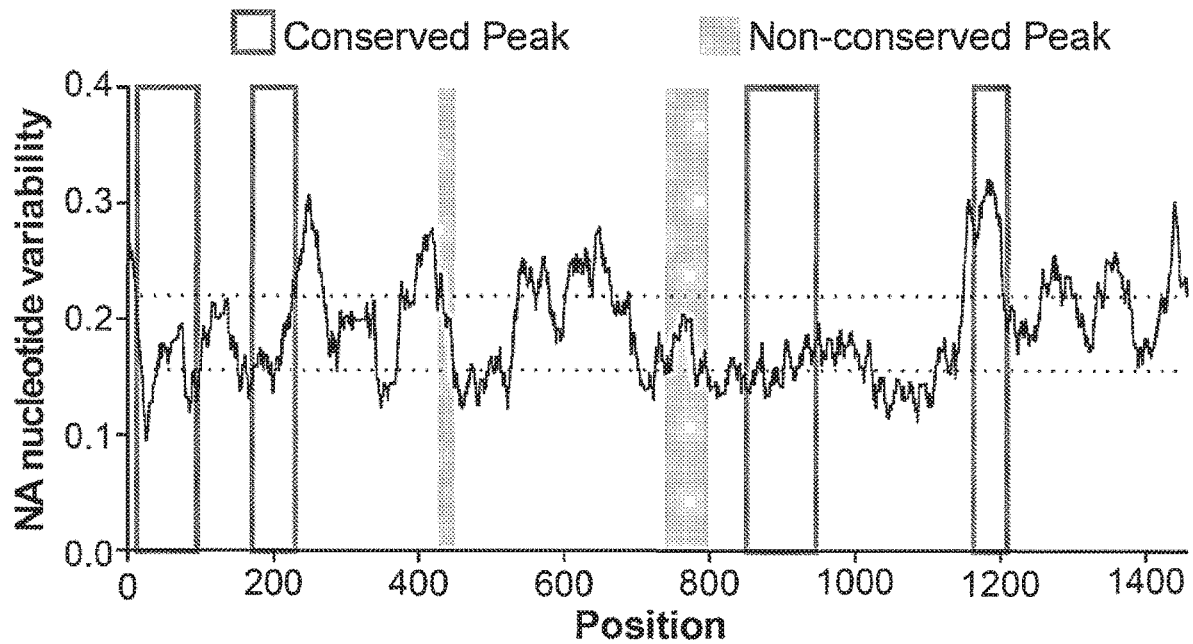

Further studies were performed to investigate the underlying determinant of NP association and examine whether peaks have a conserved sequence to direct NP binding. Motif enrichment in the peak vRNA sequences was analyzed using the MEME suite (Bailey and Elkan, *Proc Int Conf Intell Syst Mol Biol* 1:28-36, 1994; Ma et al., *Nat Protoc* 9(6):1428-1450, 2014), but no obvious motif was found, confirming previous observations that NP binds vRNA without sequence specificity (Baudin et al., *EMBO J* 13(13):3158-3165, 1994). It was next considered whether evolution rates of conserved and non-conserved NP-binding peaks were different. WSN and H1N1pdm are H1N1 viruses separated by over 70 years, and the error-prone viral polymerase is known to generate an average of $2.5 \times 10^{-5}$ substitutions per nucleotide site per cell infection (Nobusawa and Sato, *J Virol* 80(7):3675-3678, 2006; Parvin et al., *J Virol* 59(2): 377-383, 1986; Stech et al., *J Virol* 73(3):1878-1884, 1999; Wong et al., *Med Virol* 83(3):510-516, 2011; Drake, *Proc Natl Acad Sci USA* 90(9):4171-4175, 1993). In particular, evolution of segment 4 (HA) and 6 (NA) over seasonal epidemics is known as antigenic drift and is carefully documented for vaccine production. Therefore, it was examined whether conserved peaks within segment 4 and 6 would evolve at different rates than non-conserved peaks. The single nucleotide polymorphism (SNP) variability of these two segments was compared using an overlapping sliding window algorithm (Colson, *BMC Microbiol* 6:21, 2006; Proutski, *Bioinformatics* 14(5):467-468, 1998) for H1N1 viruses spanning the past 70 years (FIGS. 5A and 5B). The conserved peak regions of the vRNA between WSN and H1N1pdm are indicated (highlighted in red); peaks found in one but not both strains (non-conserved peaks) are denoted (gray-shaded boxes). Most conserved peaks for segment 4 (HA) had a lower SNP variability, while non-conserved peaks had both low and high SNP variability (FIG. 5A). In contrast, the SNP pattern of conserved and non-conserved peaks for segment 6 (NA) was not consistent and had both low and high SNP variability (FIG. 5B). Therefore, no concrete conclusions can be drawn regarding molecular evolution and NP binding.

The nucleotide contents of peak and non-peak regions in all strains were next analyzed and compared to the overall genome-wide content (FIG. 5C and Table 3). Interestingly, peaks were significantly enriched in guanine (G) residues compared to the overall content (22.4% compared to 18.8%), while uracil (U) bases were relatively depleted (30.2% compared to 34.0%; chi-squared test p-value >0.0001) (FIG. 5C and Table 3). Conversely, within non-peak regions, U residues increased to 36.8%, while G residues decreased to 16.2% (FIG. 5C and Table 3). This trend was observed for all individual influenza virus strains (Table 3). The content of A and C bases were maintained at approximately 23% in both populations. Taken together, these data suggest that NP trimers preferably associate with relatively G-rich and low U-containing regions of vRNA.

TABLE 3

Average nucleotide content of vRNA regions categorized as NP-peaks and non-peaks

| Virus | Nucleotide | Total Genome | Peaks | Non-Peaks |
|---|---|---|---|---|
| WSN | A | 23.7% | 23.2% ± 5.5 | 24.2% ± 5.1 |
|  | U | 32.9% | 28.9% ± 7.7 | 34.2% ± 5.2 |
|  | G | 19.2% | 23.9% ± 5.1 | 17.5% ± 4.3 |
|  | C | 24.3% | 23.9% ± 4.9 | 24.0% ± 5.4 |
| H1N1pdm | A | 23.1% | 23.1% ± 4.4 | 23.3% ± 6.0 |
|  | U | 33.5% | 29.9% ± 4.9 | 37.4% ± 5.9 |
|  | G | 19.3% | 22.4% ± 3.9 | 16.5% ± 3.3 |
|  | C | 24.1% | 24.6% ± 5.1 | 22.8% ± 5.5 |
| Seasonal H3N2 | A | 23.6% | 23.5% ± 5.8 | 24.4% ± 7.8 |
|  | U | 33.4% | 31.1% ± 5.8 | 39.2% ± 6.9 |
|  | G | 19.2% | 22.0% ± 3.6 | 15.1% ± 5.1 |
|  | C | 23.8% | 23.4% ± 5.2 | 21.2% ± 7.4 |
| IVB | A | 23.5% | 24.7% ± 6.2 | 23.6% ± 5.4 |
|  | U | 36.0% | 32.0% ± 5.8 | 37.3% ± 4.9 |
|  | G | 17.8% | 20.7% ± 4.8 | 17.4% ± 5.0 |
|  | C | 22.7% | 22.6% ± 4.4 | 21.6% ± 4.9 |
| All Strains | A | 23.4% | 23.8% ± 5.5 | 23.7% ± 6.0 |
|  | U | 34.0% | 30.1% ± 6.2 | 36.9% ± 6.0 |
|  | G | 18.9% | 22.3% ± 4.5 | 16.7% ± 4.5 |
|  | C | 23.7% | 23.8% ± 4.8 | 22.9% ± 5.9 |

Summary

Disclosed herein are the first global maps of association between NP and vRNA for different strains of IAV and IBV. These studies contribute significantly to the field's understanding of vRNP structure. The prevailing dogma in the field has been that NP associates with vRNA similar to 'beads on a string' in a random and uniform manner; however, the data disclosed herein demonstrate that this is not the case and that there are regions of the vRNA that are strongly associated with NP (peaks) and regions with little to no NP binding, where the RNA-seq coverage is similar to background. The presence of NP-free regions is consistent with data from a cryo-EM study suggesting that some regions of vRNA are exposed due to spacing gaps within helical reconstruction of NP molecules (Moeller et al., *Science* 338(6114):1631-1634, 2012).

All of the viruses studied (3 IAV and 1 IBV) have different NP-vRNA binding profiles. By comparing these profiles among strains (see Pearson correlations in Table 2), it was observed that the similarity between H1N1 strains (WSN compared to H1N1pdm) was the same as that between H1N1 and H3N2 strains. By contrast, the profile of IBV NP-vRNA association was strikingly different than any IAV, which, apart from sequence divergence, may also be attributed to the structural differences between IAV and IBV NP. IBV NP lacks two nuclear localization signals that are present in IAV NP and contains 50 additional amino acids in its N-terminal domain that are not found in IAV (Stevens and Barclay, *J Virol* 72(6):5307-5312, 1998), which facilitates the formation of high-level oligomers and IBV RNA-NP complexes (Liu et al., *PLoS One* 10(9):e0137802, 2015).

Figure 6:
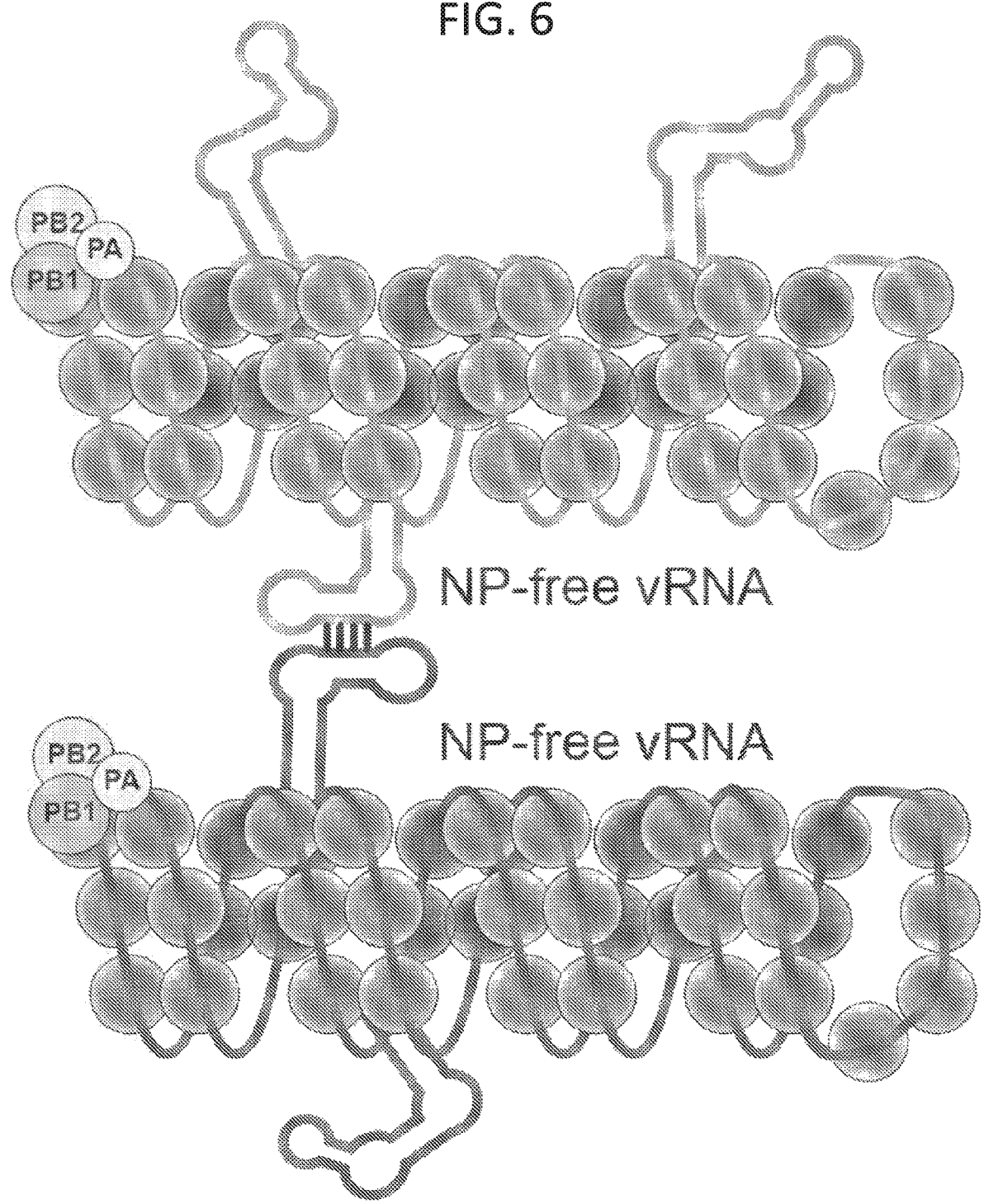
FIG. 6: Schematic of a proposed model depicting NP-free, accessible regions of vRNA engaging in potential RNA-RNA interactions.
Figure 7A:
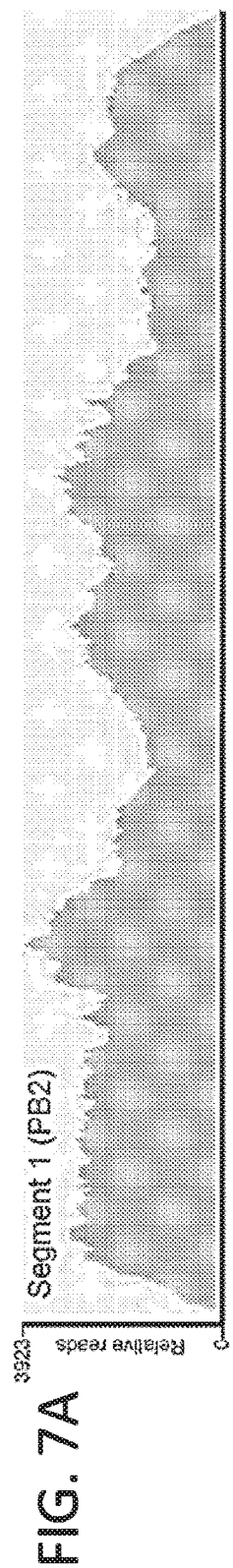
FIGS. 7A-7H: Inputs for WSN. RNA was extracted from purified virions and all eight segments were deep sequenced to ensure proper coverage of the entire genome was achievable.
Figure 7B:
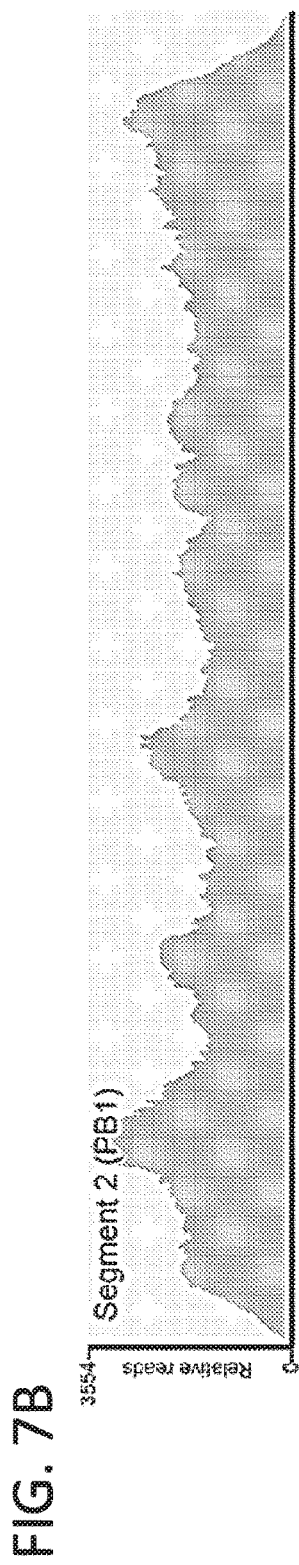
Figure 7C:
Figure 7D:
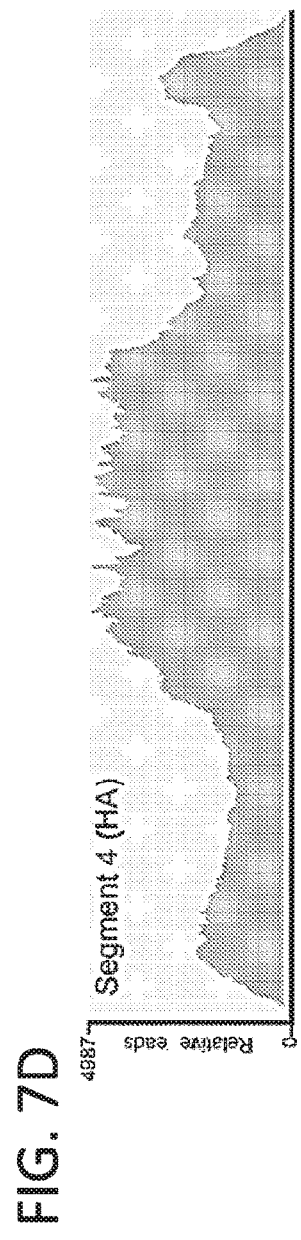
Figure 7E:
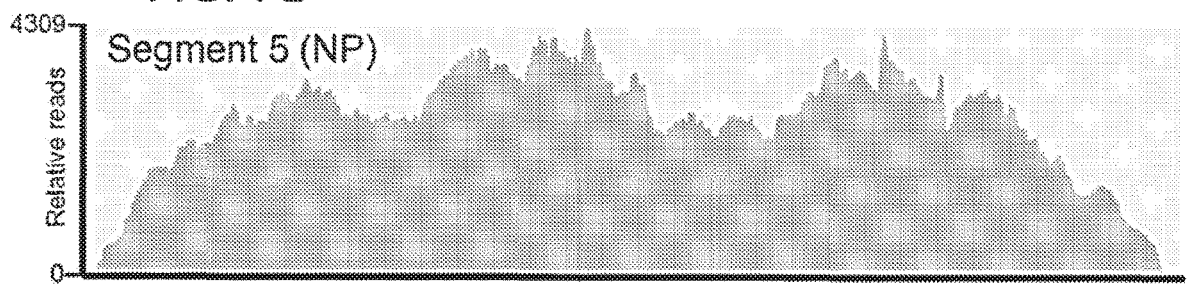
Figure 7F:
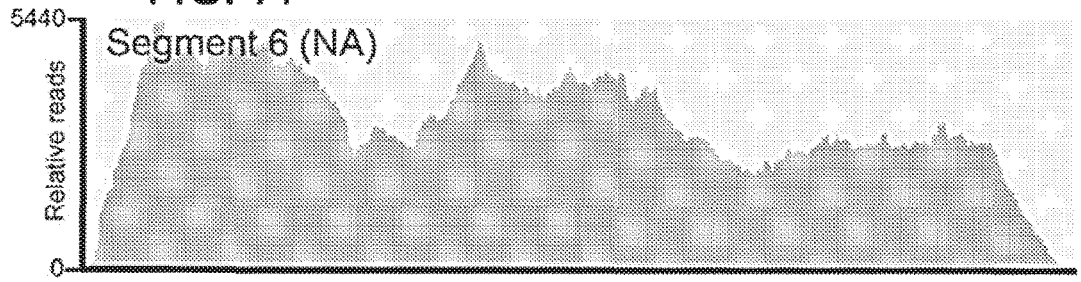
Figure 7G:
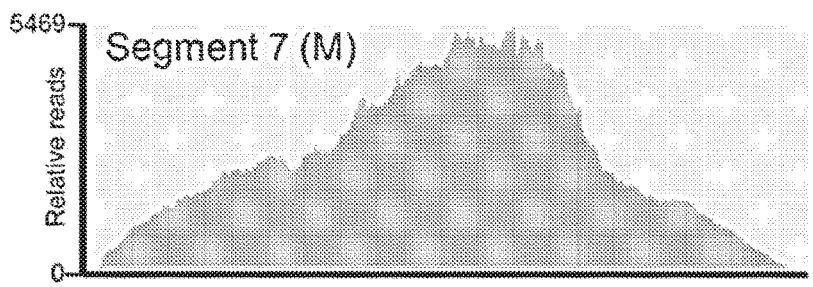
Figure 7H:
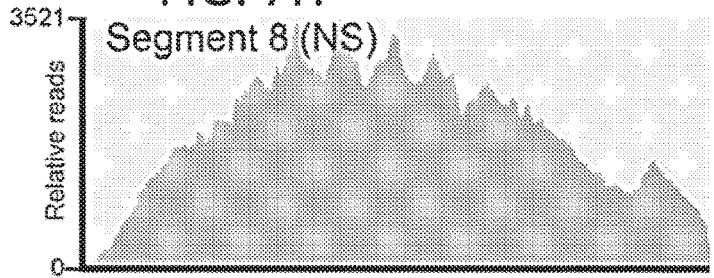

As previously shown (Baudin et al., *EMBO J* 13(13):3158-3165, 1994), no RNA sequence motif underlying NP association was identified. However, the data suggest that vRNA nucleotide content may be driving the degree of IAV and IBV NP association (FIG. 5C). Intriguingly, it was observed that G bases are relatively enriched in NP binding sites as compared to genome-wide G bases content. In contrast, U bases were relatively depleted in NP peaks; the reverse was observed for non-peak regions. The increase in U residues in the non-peaks, and propensity for U nucleotides to form wobble base pairings (Varani et al., *EMBO Rep* 1(1):18-23, 2000), may help mediate vRNA-vRNA interactions without direct sequence homology. While it is proposed herein that the NP-free vRNA regions are capable of complex RNA-RNA interactions necessary for selective assembly of all eight vRNA segments (FIG. 6), an alternative explanation may be that non-peak regions are occupied by host RNA-binding proteins incorporated into virions (Hutchinson et al., *Nat Commun* 5:4816, 2014).

In addition, three areas of vRNA were observed that were termed 'super peaks' since they were over-represented in NP HITS-CLIP and greater than 9 times the maximum normalized peak height. These 'super peaks' were contained in segment 6 (NA) of H1N1pdm and IBV and another in segment 7 (M) of IBV. The super peaks found in segment 6 (NA) for both H1N1pdm and IBV were not at the same location.

Structural studies provide a model in which the vRNPs form an anti-parallel, NP-coated double helix with the polymerase complex at one end and an NP-covered loop at the other (Arranz et al., *Science* 338(6114):1634-1637, 2012; Moeller et al., *Science* 338(6114):1631-1634, 2012). UV-crosslinking experiments indicate that the polymerase complex interacts with the 5' and 3' ends of the vRNAs (Fodor et al., *J Virol* 68(6):4092-4096, 1994; Fodor et al., *J Gen Virol* 74 (Pt 7):1327-1333, 1993). Recent crystal structures of the polymerase complex with short RNAs demonstrate that nucleotides 1-10 of the 5' end form a compact stem-loop within a deep pocket at the interface of PB1 and PA, while nucleotides 1-9 of the 3' end bind to the surface of the polymerase (Hengrung et al., *Nature* 527(7576):114-117, 2015; Pflug et al., *Nature* 516(7531):355-360, 2014; Reich et al., *Nature* 516(7531):361-366, 2014), suggesting that the vRNA termini should be devoid of NP, as they are occupied by the polymerase complex. Unexpectedly, the studies disclosed herein determined that not all 5' and 3' ends lack NP association. For example, the 3' end of segment 5 (NP) from H1N1pdm and H3N2 each have a strong peak as well as the 3' end of segment 7 (M) from IBV, which presents as a super peak.

The segmented nature of the influenza virus genome provides challenges for selective assembly as well as an evolutionary advantage to the virus by facilitating genetic reassortment. It also contributes to the emergence of novel pandemic strains, as evidenced by co-segregating vRNA segments (Cobbin et al., *J Virol* 88(16):8971-8980, 2014; Jackson et al., *J Virol* 83(16):8131-8140, 2009; Octaviani et al., *J Virol* 84(20):10918-10922, 2010). Understanding reassortment between influenza viruses is critical for predicting emerging influenza pandemics. Since a genetic reassortment bias has been described in the literature, the HITS-CLIP data disclosed herein provides insight into this reassortment bias. Previously, in vitro binding assays have identified specific areas of vRNA segments that can interact with other vRNA segments (Essere et al., *Proc Natl Acad Sci USA* 110(40):E3840-3848, 2013; Fournier et al., *Vaccine* 39(51):7359-7367, 2012; Fournier et al., *Nucleic Acids Res* 40(5):2197-2209, 2012; Gavazzi et al., *Nucleic Acids Res* 41(2):1241-1254, 2013; Gavazzi et al., *Proc Natl Acad Sci USA* 110 (41):16604-16609, 2013; Noda et al., *Nat Commun* 3:639, 2012). Many of the regions responsible for vRNA-vRNA interaction were located within the coding region for avian H5N2 (A/Finch/England/205/91.) virus (Fournier et al., *Nucleic Acids Res* 40(5):2197-2209, 2012; Gavazzi et al., *Nucleic Acids Res* 41(2):1241-1254, 2013). However, these studies were performed on naked RNA without NP. Based on the distinct association of NP to the vRNA segments, the addition of NP might alter the availability of vRNA segments capable of base pairing. A recent study using vRNPs from a H3N2 (A/Udorn/307/72) virus found that segment 2 (PB1) between nucleotides 1776 and 2070 interacted with segment 6 (NA), which drives co-segregation of these two segments in the virus (Gilbertson et al., *Viruses* 8(8), 2016). In the NP-vRNA binding profile of H3N2 disclosed herein, segment 2 (PB1) contains two NP-free regions and one of these lies within nucleotides 1776-2070 (FIG. 3, black arrowhead). Therefore, conserved NP-free regions may not only provide insight into the vRNA regions mediating the direct RNA-RNA interaction (FIG. 6), but may also help predict the reassortment potential of certain vRNA segments. If NP-free regions are important for reassortment, the striking differences in NP-vRNA association between IAV and IBV may provide an explanation as to why IAV and IBV are incapable of reassortment. Alternatively, segments with highly similar NP binding patterns may be interchangeable and more likely to be packaged with segments from different strains in a co-infected cell.

Example 3: Sequences of Antisense Oligonucleotides Targeting Genomic Regions of Influenza a Strains This example describes antisense oligonucleotides that target highly conserved regions of the influenza A virus genome, which were designed in order to interfere with replication of a wide range of different influenza A virus strains.

The six antisense oligonucleotides shown below are complementary to influenza nucleoprotein (NP) binding sites in the genome that are conserved in sequence in the three influenza A virus (JAY) strains examined (see Examples 1 and 2). Conserved regions were chosen so that the ASOs would target multiple different IAV strains.

```
SEQ ID NO: 1 targets the PB2 gene (segment 1):
GCATACTTACTGACAGCCAGACAGCGACCAAAAGAATTCGGATGGCCATC
(50 nt)

SEQ ID NO: 2 targets the polymerase (PA) gene
(segment 3):
AATGCTTCTTGGTTCAACTCCTTCCTCACACATGCA (36 nt)

SEQ ID NO: 3 targets the NS1/NS2 genes (segment 8):
TGAGGATGTCAAAAATGCAGTTGGGGTCCTCATCGGAGG (39 nt)

SEQ ID NO: 4 targets the NS1/NS2 genes (segment 8):
GAAATTTCACCACTGCCCTCTCTTCCAGGACATACTGA (38 nt)

SEQ ID NO: 5 targets the M1/M2 genes (segment 7):
AACAGATTGCTGACTCCCAGCATCGGTCTCATAGGCAAATGG (42 nt)

SEQ ID NO: 6 targets the polymerase (PA) gene
(segment 3):
CACATTTTCTCATTCACTGGGGAGGAAATGGCCAC (35 nt)
```

In addition to the full ASO sequences listed above, ASOs that include at least 20, at least 25 or at least 30 consecutive nucleotides of any of the above sequences can be used to inhibit IAV. For example, the ASO ACAGCCA-GACAGCGACCAAAAGAAT is a 25-mer portion (nucleotides 13-37) of SEQ ID NO: 1. ASOs are generally selected to have moderate GC content (~40-50%), to not self-anneal, and have no major homology to host/human RNA sequences.

In some instances, the ASOs include chemical modifications, such as 2'-O-methylated nucleotides and/or a phosphorothioate backbone. In some cases, the ASOs are morpholino oligonucleotides or PNAs.

Antisense oligonucleotides are tested in assays of influenza virus replication to test efficacy. ASO are transfected into transformed cell lines such as A549 and/or MDCK cells, using commercially available transection reagents. Briefly, either a single ASO or a cocktail of ASOs is introduced into A549 or MDCK cells using a lipid-based transfection reagent. Approximately 8 hours post-transfection, the cells are infected with influenza virus and the supernatant is collected at 8, 12, 16, 24, 48 and 72 hours post-infection to determine the impact of ASO on viral replication. The amount of infectious virus particles is determined in the supernatants by plaque assay or tissue culture infectious dose 50. Viral replication in cells treated with ASO specific to NP-vRNA peaks is compared to irrelevant ASO. Similar studies are performed to test the efficacy of ASO treatment after viral infection. Additional studies are performed to study the impact of ASO on airway epithelial cells grown at an air-liquid interface. ASO can be introduced in these cell types using nanoparticles, such as by following the procedure of McNeer et al. (*Nat Commun* 6:6952, 2015).

Example 4: Antisense Oligonucleotides Targeting Conserved NP-vRNA Peak Regions Limit Influenza Virus Infection This example describes a study to test the ability of four antisense oligonucleotides that target conserved NP-vRNA peak regions to limit influenza virus infection.

293 T Cells were transfected with a combination of two antisense oligonucleotides (SEQ ID NOs: 1 and 2), transfected with a non-specific oligonucleotide (transfection control) or were left untransfected. Four hours later, transfected and non-transfected cells were infected with H1N1 influenza virus WSN. Cell culture media was replaced four hours post-infection. At 24 hours post-infection, cell culture supernatant was collected and virus titer was determined on MDCK cells.

Figure 9:
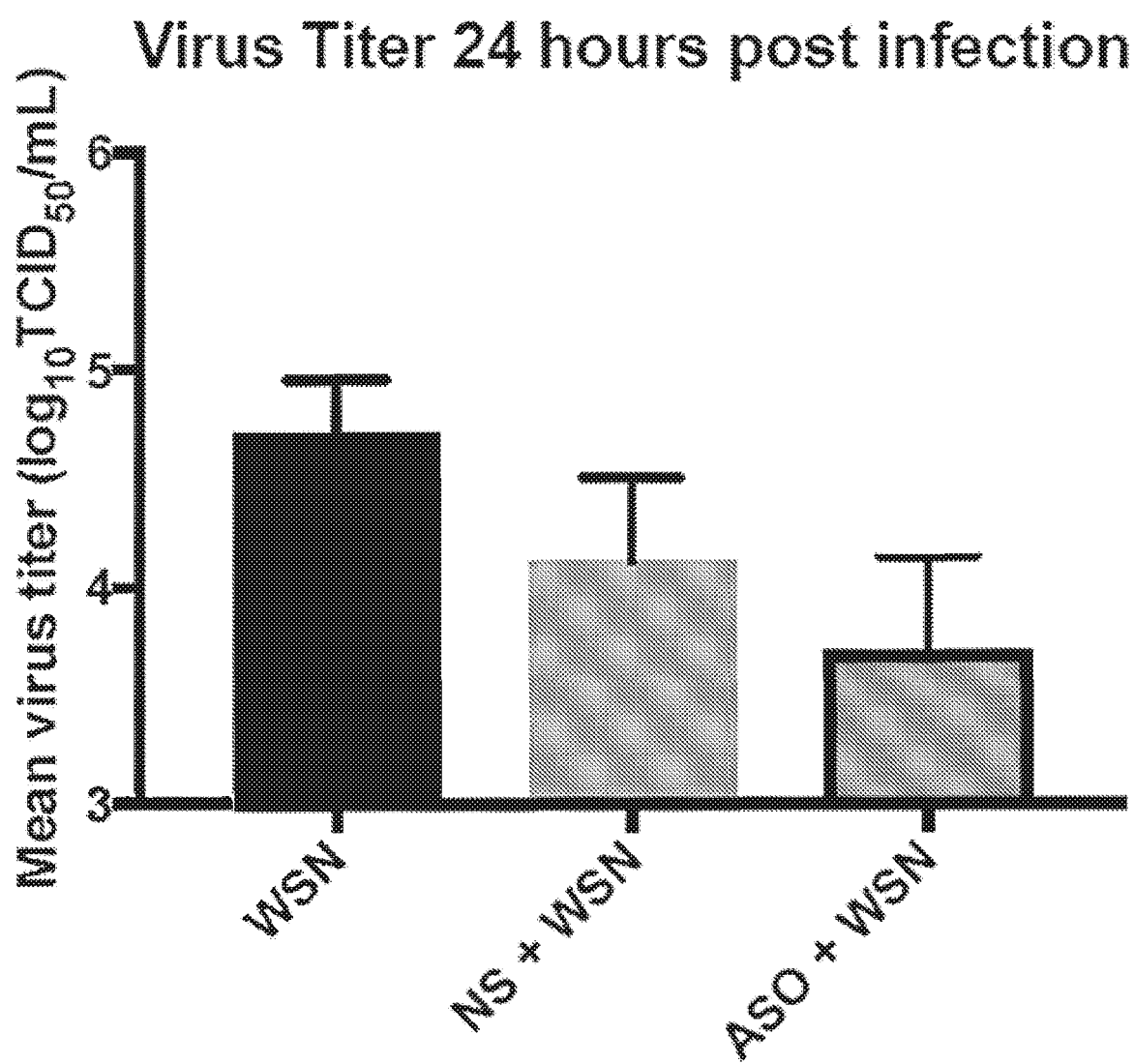
FIG. 9: Antisense oligonucleotides targeting conserved NP-vRNA peak regions limit influenza virus infection. 293 T Cells were transfected with a combination of two antisense oligonucleotides (ASO) (SEQ ID NOs: 1 and 2), transfected with a non-specific (NS) oligonucleotide or were left untransfected. Four hours later, transfected and non-transfected cells were infected with H1N1 influenza virus WSN. Cell culture media was replaced four hours post-infection. At 24 hours post-infection, cell culture supernatant was collected and virus titer was determined on MDCK cells. Each condition was performed in triplicate, with the mean and standard deviation represented.

As shown in FIG. 9, transfection with influenza-specific antisense oligonucleotides decreased virus titer relative to cells transfected with a control oligonucleotide and untransfected cells.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A composition comprising a pharmaceutically acceptable carrier and at least one antisense oligonucleotide (ASO) selected from:
   an ASO having at least 90% sequence identity with SEQ ID NO: 1;
   an ASO having at least 90% sequence identity with SEQ ID NO: 2;
   an ASO having at least 90% sequence identity with SEQ ID NO: 3;
   an ASO having at least 90% sequence identity with SEQ ID NO: 4;
   an ASO having at least 90% sequence identity with SEQ ID NO: 5;
   an ASO having at least 90% sequence identity with SEQ ID NO: 6;
   an ASO comprising at least 20 consecutive nucleotides of SEQ ID NO: 1;
   an ASO comprising at least 20 nucleotides of SEQ ID NO: 2;
   an ASO comprising at least 20 consecutive nucleotides of SEQ ID NO: 3;
   an ASO comprising at least 20 consecutive nucleotides of SEQ ID NO: 4;
   an ASO comprising at least 20 consecutive nucleotides of SEQ ID NO: 5; and
   an ASO comprising at least 20 consecutive nucleotides of SEQ ID NO: 6,
   wherein the at least one ASO comprises one or more chemical modifications.

2. The composition of claim 1, wherein the at least one ASO is selected from:
   an ASO no more than 55 nucleotides in length comprising SEQ ID NO: 1;
   an ASO no more than 40 nucleotides in length comprising SEQ ID NO: 2;
   an ASO no more than 43 nucleotides in length comprising SEQ ID NO: 3;
   an ASO no more than 42 nucleotides in length comprising SEQ ID NO: 4;
   an ASO no more than 46 nucleotides in length and comprising SEQ ID NO: 5; and
   an ASO no more than 38 nucleotides in length comprising SEQ ID NO: 6.

3. The composition of claim 1, wherein the at least one ASO is selected from:
   an ASO having a nucleotide sequence consisting of SEQ ID NO: 1;

an ASO having a nucleotide sequence consisting of SEQ ID NO: 2;
an ASO having a nucleotide sequence consisting of SEQ ID NO: 3;
an ASO having a nucleotide sequence consisting of SEQ ID NO: 4;
an ASO having a nucleotide sequence consisting of SEQ ID NO: 5; and
an ASO having a nucleotide sequence consisting of SEQ ID NO: 6.

4. The composition of claim 1, wherein the at least one ASO is selected from:
an ASO comprising at least 25 consecutive nucleotides of SEQ ID NO: 1;
an ASO comprising at least 25 consecutive nucleotides of SEQ ID NO: 2;
an ASO comprising at least 25 consecutive nucleotides of SEQ ID NO: 3;
an ASO comprising at least 25 consecutive nucleotides of SEQ ID NO: 4;
an ASO comprising at least 25 consecutive nucleotides of SEQ ID NO: 5; and
an ASO comprising at least 25 consecutive nucleotides of SEQ ID NO: 6.

5. The composition of claim 4, wherein the at least one ASO is selected from:
an ASO comprising at least 30 consecutive nucleotides of SEQ ID NO: 1;
an ASO comprising at least 30 consecutive nucleotides of SEQ ID NO: 2;
an ASO comprising at least 30 consecutive nucleotides of SEQ ID NO: 3;
an ASO comprising at least 30 consecutive nucleotides of SEQ ID NO: 4;
an ASO comprising at least 30 consecutive nucleotides of SEQ ID NO: 5; and
an ASO comprising at least 30 consecutive nucleotides of SEQ ID NO: 6.

6. The composition of claim 1, comprising at least 2 ASOs selected from:
an ASO having at least 90% sequence identity with SEQ ID NO: 1;
an ASO having at least 90% sequence identity with SEQ ID NO: 2;
an ASO having at least 90% sequence identity with SEQ ID NO: 3;
an ASO having at least 90% sequence identity with SEQ ID NO: 4;
an ASO having at least 90% sequence identity with SEQ ID NO: 5; and
an ASO having at least 90% sequence identity with SEQ ID NO: 6.

7. The composition of claim 1, comprising at least 3 ASOs selected from:
an ASO having at least 90% sequence identity with SEQ ID NO: 1;
an ASO having at least 90% sequence identity with SEQ ID NO: 2;
an ASO having at least 90% sequence identity with SEQ ID NO: 3;
an ASO having at least 90% sequence identity with SEQ ID NO: 4;
an ASO having at least 90% sequence identity with SEQ ID NO: 5; and
an ASO having at least 90% sequence identity with SEQ ID NO: 6.

8. The composition of claim 1, comprising at least 4 ASOs selected from:
an ASO having at least 90% sequence identity with SEQ ID NO: 1;
an ASO having at least 90% sequence identity with SEQ ID NO: 2;
an ASO having at least 90% sequence identity with SEQ ID NO: 3;
an ASO having at least 90% sequence identity with SEQ ID NO: 4;
an ASO having at least 90% sequence identity with SEQ ID NO: 5; and
an ASO having at least 90% sequence identity with SEQ ID NO: 6.

9. The composition of claim 1, comprising:
an ASO having at least 90% sequence identity with SEQ ID NO: 1;
an ASO having at least 90% sequence identity with SEQ ID NO: 2;
an ASO having at least 90% sequence identity with SEQ ID NO: 3;
an ASO having at least 90% sequence identity with SEQ ID NO: 4;
an ASO having at least 90% sequence identity with SEQ ID NO: 5; and
an ASO having at least 90% sequence identity with SEQ ID NO: 6.

10. The composition of claim 1, comprising:
an ASO having a nucleotide sequence consisting of SEQ ID NO: 1; and
an ASO having a nucleotide sequence consisting of SEQ ID NO: 2.

11. The composition of claim 1, wherein the at least one ASO comprises at least one modification that increases nuclease resistance and/or increases binding affinity.

12. The composition of claim 1, wherein the at least one ASO comprises at least one phosphorothioate, at least one 2'-fluoro, at least one 2'-O-methyl, at least one 2'-O-methoxy-ethyl, at least one morpholino and/or at least one locked nucleic acid (LNA).

13. The composition of claim 1, wherein the at least one ASO is formulated for oral, inhalation or parenteral administration.

14. A method of inhibiting replication of an influenza A virus in a host cell, comprising contacting the cell with the composition of claim 1.

15. The method of claim 14, wherein the method is an in vitro method.

16. The method of claim 14, wherein the method is an in vivo method wherein contacting the cell comprises administering the composition to a subject infected with an influenza A virus.

17. A method of treating an influenza A virus infection in a subject, comprising administering to the subject the composition of claim 1.

18. The method of claim 17, further comprising administering to the subject a second influenza antiviral therapeutic agent.

19. The method of claim 18, wherein the influenza antiviral therapeutic agent comprises oseltamivir, zanamivir, peramivir, amantadine or rimantadine.

20. A method of inhibiting replication of an influenza A virus in a host cell, comprising contacting the cell with a composition comprising a pharmaceutically acceptable carrier and at least one antisense oligonucleotide (ASO) selected from:

an ASO having at least 90% sequence identity with SEQ ID NO: 1;
an ASO having at least 90% sequence identity with SEQ ID NO: 2;
an ASO having at least 90% sequence identity with SEQ ID NO: 3;
an ASO having at least 90% sequence identity with SEQ ID NO: 4;
an ASO having at least 90% sequence identity with SEQ ID NO: 5;
an ASO having at least 90% sequence identity with SEQ ID NO: 6;
an ASO comprising at least 20 consecutive nucleotides of SEQ ID NO: 1;
an ASO comprising at least 20 nucleotides of SEQ ID NO: 2;
an ASO comprising at least 20 consecutive nucleotides of SEQ ID NO: 3;
an ASO comprising at least 20 consecutive nucleotides of SEQ ID NO: 4;
an ASO comprising at least 20 consecutive nucleotides of SEQ ID NO: 5; and
an ASO comprising at least 20 consecutive nucleotides of SEQ ID NO: 6.

* * * * *

SEQUENCE LISTING

<160> NUMBER OF SEQ ID NOS: 11

<210> SEQ ID NO 1
<211> LENGTH: 50

-continued

```
<212> TYPE: DNA
<213> ORGANISM: Artificial Sequence
<220> FEATURE:
<223> OTHER INFORMATION: Synthetic oligonucleotide

<400> SEQUENCE: 1
gcatacttac tgacagccag acagcgacca aaagaattcg gatggccatc                50

<210> SEQ ID NO 2
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 2
aatgcttctt ggttcaactc cttcctcaca catgca                                36

<210> SEQ ID NO 3
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 3
tgaggatgtc aaaaatgcag ttggggtcct catcggagg                             39

<210> SEQ ID NO 4
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 4
gaaatttcac cactgccctc tcttccagga catactga                              38

<210> SEQ ID NO 5
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 5
aacagattgc tgactcccag catcggtctc ataggcaaat gg                         42

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 6
cacattttct cattcactgg ggaggaaatg gccac                                 35

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 7
```

-continued

```
ctcatgctct accgactgag ctagccgggc                                    30

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
ccttgaactg agaagcagat act                                           23

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
tgtatggatc tgccgtagcc agtg                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
tttgaatgat gcaacttacc agag                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
aggaataaat atctagaaga acat                                          24
```